(12) United States Patent
Fisher et al.

(10) Patent No.: US 7,744,930 B2
(45) Date of Patent: Jun. 29, 2010

(54) COMPOSITIONS, METHODS AND KITS FOR ENHANCING WEIGHT LOSS WHILE INHIBITING LOSS OF LEAN BODY MASS

(75) Inventors: Laurel Fisher, San Francisco, CA (US); Jamie McManus, Pleasanton, CA (US); Kathleen Taylor, Berkeley, CA (US); Haruna Yamaguchi, Hayward, CA (US)

(73) Assignee: Shaklee Corporation, Pleasanton, CA (US)

( * ) Notice: Subject to any disclaimer, the term of this patent is extended or adjusted under 35 U.S.C. 154(b) by 0 days.

(21) Appl. No.: 11/452,004

(22) Filed: Jun. 12, 2006

(65) Prior Publication Data

US 2006/0275506 A1    Dec. 7, 2006

Related U.S. Application Data

(63) Continuation-in-part of application No. 10/722,368, filed on Nov. 24, 2003, now abandoned.

(60) Provisional application No. 60/428,993, filed on Nov. 22, 2002.

(51) Int. Cl.
*A61K 36/00* (2006.01)
(52) U.S. Cl. ..................................................... 424/725
(58) Field of Classification Search ........................ None
See application file for complete search history.

(56) References Cited

U.S. PATENT DOCUMENTS

| 5,167,957 | A | 12/1992 | Webb, Jr. et al. |
| 5,273,754 | A | 12/1993 | Mann |
| 5,378,480 | A | 1/1995 | Carieri |
| 5,514,656 | A | 5/1996 | Cope et al. |
| 5,612,039 | A | 3/1997 | Policappelli et al. |
| 5,614,553 | A | 3/1997 | Ashmead et al. |
| 5,858,449 | A | 1/1999 | Crank et al. |
| 5,891,925 | A | 4/1999 | Behr |
| 5,985,339 | A | 11/1999 | Kamarei |
| 6,140,304 | A | 10/2000 | Sears |
| 6,150,399 | A | 11/2000 | Patel et al. |
| 6,221,836 | B1 | 4/2001 | Beale et al. |
| 6,268,011 | B1 | 7/2001 | Hoie |
| 6,387,883 | B1 | 5/2002 | Abbruzzese et al. |
| 6,521,591 | B1 * | 2/2003 | Smeets et al. .................. 514/2 |
| 6,572,876 | B2 | 6/2003 | Waggle et al. |
| 6,784,206 | B2 | 8/2004 | Udell et al. |
| 6,869,621 | B2 | 3/2005 | Hwang et al. |
| 2002/0197331 | A1 | 12/2002 | Komorowski et al. |
| 2004/0071825 | A1* | 4/2004 | Lockwood .................. 426/72 |
| 2004/0087490 | A1 | 5/2004 | Troup et al. |
| 2004/0166181 | A1 | 8/2004 | Hegenauer et al. |
| 2006/0045906 | A1 | 3/2006 | Gardiner et al. |
| 2006/0205633 | A1* | 9/2006 | Nishitani et al. ................ 514/3 |

FOREIGN PATENT DOCUMENTS

| EP | 1552753 | 7/2005 |
| JP | 09227398 | 9/1997 |
| WO | WO2004/026294 | 1/2004 |
| WO | WO2004/047765 | 6/2004 |
| WO | WO 2005/049006 | * 6/2005 |

OTHER PUBLICATIONS

Green Tea Fat Burner website (http://web.archive.org/web/20040923041045/http://www.vitsdirect.co.uk/products/green.tea.fat.burner.htm—web archive version from Sep. 23, 2004).*
Physicallyelite.com (http://web.archive.org/web/20050320074844/http://www.physicallyelite.com/store/store.cfm?do=detail&product_id=13055—web archive version from Mar. 2005).*
Bushkin et al. (Health Products Business (Jun. 2001), vol. 47, No. 6, pp. 38).*
http://www.archive.org/about/faqs.php—accessed Jul. 2008.*
http://dictionary.reference.com/browse/a—accessed Jul. 2008.*
Crozier et al., *Oral Leucine Administration Stimulates Protein Synthesis in Rat Skeletal Muscle*, J. Nutr., 135:376-382 (2005).
Gallagher et al., *β-hydroxy-β-methylbutyrate Ingestion, Part II: Effects on Hematology, Hepatic and Renal Function*, Med. & Sci. in Sports & Exer., 32(12):2116-2119 (2000).
Garlick, *The Role of Leucine in the Regulation of Protein Metabolism*, J. Nutr., 135:1553S-1556S (2005).
Halton & Hu, *The Effects of High Protein Diets on Thermogenesis, Satiety and Weight Loss: A Critical Review*, J. Am. Coll. Nutr., 23(5):373-85 (2004).
Hill and Blundell, *Macronutrients and Satiety: The Effects of a High-protein or High-Carbohydrate Meal on Subjective Motivation to Eat and Food Preferences*, Nutr. Behav., 3:133-144 (1986).
Karlsson et al., *Branched-chain Amino Acids Increase $p70^{S6k}$ Phosphorylation in Human Skeletal Muscle after Resistance Exercise*, Am. J. Physiol. Endocrinol. Metab., 287: E1-E7 (2004).
Kim et al., *Lipid-lowering Efficacy of 3,4-di(OH)-phenylpropionic L-leucine in High-cholesterol Fed Rats*, J. Biochem. & Molec. Tox., 19(1):25-31 (2005).
Koopman et al., *Combined Ingestion of Protein and Free Leucine with Carbohydrate Increases Postexercise Muscle Protein Synthesis in vivo in Male Subjects*, Am. J. Physiol. Endocrinol. Metab., 288:E645-E653 (2005).

(Continued)

*Primary Examiner*—Patricia Leith
(74) *Attorney, Agent, or Firm*—Klarquist Sparkman, LLP

(57) ABSTRACT

Disclosed are combinations of soy protein, chromium and free leucine in amounts effective to inhibit the loss of lean body mass of a subject under conditions of caloric restriction. The soy protein, chromium and free leucine can be administered in several products, including a powder that is mixable into a liquid beverage (such as a shake), a snack bar, and a nutritional supplement (such as one or more tablets). Some embodiments also include corosolic acid and/or a tea drink that provides an effective dose of taurine. The products may be contained in kits containing the disclosed combinations as well as methods of using the products for weight loss and the inhibition of the loss of lean body mass in a subject during weight loss. The products and methods are also useful in the improvement of lipid profiles (for example reducing total cholesterol and LDL cholesterol levels).

6 Claims, No Drawings

OTHER PUBLICATIONS

Layman et al., *A Reduced Ratio of Dietary Carbohydrate to Protein Improves Body Composition and Blood Lipid Profiles During Weight Loss in Adult Women*, J. Nutri., 133:411-417 (2003).

Layman, *The Role of Leucine in Weight Loss Diets and Glucose Homeostasis*, J. Nutr., 133:261S-267S (2003).

Matthews, *Observations of Branched-chain Amino Acid Administration in Humans*, J. Nutr., 135:1580S-1584S (2005).

Mourier et al., *Combined Effects of Caloric Restriction and Branched-chain Amino Acid Supplementation on Body Composition and Exercise Performance in Elite Wrestlers*, Int. J. Sports Med., 18:47-55 (1997).

Nair & Short, *Hormonal and Signaling Role of Branched-chain Amino Acids*, J. Nutr., 135:1547S-1552S (2005).

Weigle et al., *A High-protein Diet Induces Sustained Reductions in Appetite, ad libitum Caloric Intake, and Body Weight Despite Compensatory Changes in Diurnal Plasma Leptin and Ghrelin Concentrations*, Am. J. Clin. Nutr., 82:41-8 (2005).

Unknown, *Clinical Study Shows Glucosol Is Effective in Reducing Blood Glucose Levels* (available at www.realfoodnutrients.com/d5/glucosolstudy.pdf as early as Oct. 2004).

Label for Shaklee "Slim Plan Drink Mix" that was the product used in the study disclosed in the Hagan publication (1986) previously cited in the IDS dated Oct. 8, 2007 and submitted in U.S. Appl. No. 10/722,368 in the IDS dated Feb. 7, 2005.

AIM SlimMetrix (visited Nov. 12, 2002) <http://www.feelhealthynow.com/weight/slimmetrix.htm>.

Anderson et al., *Cardiovascular and renal benefits of dry bean and soybean intake*, Am J Clin Nutr, 70:464S-474S (1999).

Anderson, *Review: Chromium, glucose intolerance and diabetes*, J Am Coll Nutr, 17(6):548-555 (1998).

Aoyama et al, *Effect of soy and milk whey protein isolates and their hydrosylates on weight reduction in genetically obese mice*, Biosci. Biotechnol. Biochem., 64(12):2594-2600 (2000).

Aoyama et al., *Soy protein isolate and its hydrolysate reduce body fat of dietary obese rats and genetically obese mice (Yellow KK)*, Nutrition, 16:349-354 (2000).

Bahadori et al., *Effekt von chromhefe und chrompicolinat auf die körperzusammensetzung bei übergewichtigen, nichtdiabetischen patienten während und nach einer formula-diät*, Acta Med. Austriaca, 5:185-187 (1997) (German publication with English abstract).

Becker et al., *Comparison of the effects of various vanadium salts on glucose homeostasis in streptozotocin-diabetic rats*, Eur. J. Pharmacol., 260:169-175 (1994).

Bell et al., *A functional food product for the management of weight*, Crit. Rev. Food. Sci. Nutr., 42(2):163-78 (2002) (abstract).

Bhanot et al., *Vanadyl sulfate lowers plasma insulin and blood pressure in spontaneously hypertensive rats*, Hypertension, 24(5):625-632 (1994).

Brichard et al., *The role of vanadium in the management of diabetes*, Trends Pharmacol. Sci., 16:265-270 (1995).

Cohen et al., *Oral vanadyl sulfate improves hepatic and peripheral insulin sensitivity in patients with non-insulin-dependent diabetes mellitus*, J. Clin. Invest., 95:2501-2509 (1995).

Crawford et al., *Effects of niacin-bound chromium supplementation on body composition in overweight African-American women*, Diabetes, Obesity and Metab., 1(6):331 (1999) (abstract).

EAS Myoplex Lite (vanilla cream) (visited Nov. 12, 2002) <http://www.fitnessfirstusa.com/details.asp?item+5650>.

Future Perfect (visited Nov. 12, 2002) <http://www.bodywise.com/bwcatalog/PWM104.asp>.

Goodman-Gruen et al., *Usual dietary isoflavone intake is associated with cardiovascular disease risk factors in postmenopausal women*, Journal of Nutrition, 131:1202-1206 (2001).

Grant et al, *Chromium and exercise training: effect on obese women*, Med. Sci. Sprts. Ex., pp. 992-998 (1997).

Hagan et al., *The effects of aerobic conditioning and/or caloric restriction in overweight men and women*, Med. Sci. Sprts. Ex., 18(1):87-94 (1986).

Halberstam et al., *Oral Vanadyl sulfate improves insulin sensitivity in NIDDM but not in obese nondiabetic subjects*, Diabetes, 45:659-66 (1996).

Hurley et al., *Soy protein isolate in the presence of cornstarch reduces body fat gain in rats*, Can. J. Physiol. Pharmacol., 76:1000-1007 (1998).

Jarrow Formulas Glycemic Balance (visited Nov. 12, 2002) <http://www.iherb.com/glycemic.html>.

Judy et al., *Antidiabetic Activity of a Standardized Extract (Glucosol) from Lagerstroemia Speciosa Leaves in Type II Diabetes. A Dose-Dependence Study*, J. Ethnopharmacol., 87(1):115-117 (2003).

Kaats et al., *A randomized, double-masked, placebo-controlled study of the effects of chromium picolinate supplementation on body composition: A replication and extension of a previous study*, Current Therapeutic Research, 59(6):379-388 (1998).

Kaats et al., *Effects of chromium picolinate supplementation on body composition: A randomized, double-masked, placebo-controlled study*, Current Therapeutic Research, 57(10):747-756 (1996).

Kashi GoLEAN Ready-To-Drink Shakes (visited Nov. 12, 2002) <http://www.kashi.com/prodandnutsh.html>.

Keto Soy Shakes (visited Nov. 12, 2002) <http://www.healthierways.com/soy_shakes.htm>.

Kozlovsky et al., *Effects of diets high in simple sugars on urinary chromium losses*, Metabolism, 35:515-518 (1986).

Liu et al., *An extract of Lagerstoemia speciosa L. has insulin-like glucose uptake-stimulatory and adipocyte differentiation-inhibitory activities in 3T3-L1 cells*, J. Nutr., 131:2242-2247 (2001).

Miller Pharmacal Group Cr Plus Protein (visited Nov. 12, 2002) <http://www.millerpharmacal.com/products/cr_plus_protein.html>.

Moeller et al., *Isoflavone-rich soy favorably affects regional fat and lean tissue in menopausal women*, FASEB Journal, 14 A487 (2000) (abstract).

Naturemax 'Plus' Protein Powder Strawberry (visited Nov. 12, 2002) <http://www.koshervitamns.com/cgi-bin/dbman/db.cgi?Item=MXP-30>.

Ohr, *Shedding light on weighty issues*, Foodtechnology, 56(8):125-128 (2002).

Protein Plus with Chromium Chelavite, 1 p. (product sheet from website visited Nov. 12, 2002).

Saito, *Effects of soy peptides on energy metabolism in obese animals*, Nutr. Sci. Soy Protein, Jpn., 12: 91-94 (1991).

Schoenhals, Weight Management, Natural Products Industry Insider (visited Nov. 12, 2002) <http://www.naturalproductsinsider.com/articles/261feat1.html>.

Shaklee Corporation, Craving Reduction Complex Product Brief, 3 pp. (Nov. 2003).

SlimBalance Soy Protein Meal Replacement for Fast Weight Loss (visited Nov. 12, 2002) <http://www.health4her.com/mealreplacement.cfm?adnum=sbhome>.

Slim Fast Soy Protein Shake Mix, Chocolate Delite (visited Nov. 12, 2002) <http://www.drugstore.com/qxp69522_333181_SESpider/Slim_Fast/Soy_Protein_Shake_Mi . . . >.

Suddenly Slim! Body FX (visited Oct. 27, 2004) <http://www.firstfitness.com/sudslim/about_sudslim/about_ss.asp>.

Suzuki et al., *Antiobesity activity of extracts from Lagerstroemia speciosa L. leaves on female KK-Ay mice*, J Nutr. Sci. Vitaminol (Tokyo), 45(6):791-5 (1999) (abstract).

Twinlab Ripped Fuel Thermogenic Protein Drink (visited Nov. 12, 2002) <http://www.drugstore.com/qxp31981_333181_sespider/twinlab/ripped_fuel_thermogenic_p . . . >.

Ultimate Slim Soy Protein Shakes (visited Nov. 12, 2002) <http://www.greatamericanproducts.com/p_slimsoy.html>.

Volgarev et al., *Evaluation of isolated soy protein foods in weight reduction with obese hypercholesterolemic and normocholesterolemic obese individuals*, Nutrition Reports International, 39:61-72 (1989).

Civitarese et al., *Calorie restriction increases muscle mitochondrial biogenesis in healthy humans*, PLosMed, 4(3):e76 (2007).

Krieger et al., *Effects of variation in protein and carbohydrate intake on body mass and composition during energy restriction: a meta-regression*, Am. J. Clin. Nutr., 83:260-74 (2006).

Noakes et al., *Effect of an energy restricted, high-protein, low-fat diet relative toa conventional high carbohydrate, low-fat diet on weight loss, body composition . . .* , Am. J. Clin. Nutr., 81:1298-306 (2005).

Prewitt et al, *Changes in body weight, body composition, and energy intake in women fed high- and low-fat diets*, Am. J. Clin. Nutr., 54:304-310 (1991).

Siggaard et al., *Weight loss during 12 weeks' Ad Libitum carbohydrate-rich diet in overwight and normal-weight subjects as a Danish work site*, Obesity Research, 4(4):347-356 (1996).

\* cited by examiner

COMPOSITIONS, METHODS AND KITS FOR ENHANCING WEIGHT LOSS WHILE INHIBITING LOSS OF LEAN BODY MASS

PRIORITY

This is a continuation-in-part (CIP) of U.S. patent application Ser. No. 10/722,368 filed Nov. 24, 2003 now abandoned, which claims the benefit of U.S. Provisional Application 60/428,993, filed Nov. 22, 2002.

FIELD

The disclosed products and methods concern dietary and nutritional supplements for use in weight loss programs.

BACKGROUND

Obesity has been recognized as a public health problem in the United States and throughout the world. Overweight or obese individuals are at a higher risk for developing diseases such as hypertension, dyslipidemia, type-2 diabetes (non-insulin dependent diabetes mellitus or NIDDM), coronary heart disease, stroke, gallbladder diseases, osteoarthritis, sleep apnea, and respiratory problems. Obesity is also associated with a higher prevalence of endometrial, breast, prostate and colon cancers. It is therefore not surprising that obesity is also associated with increased mortality and premature death.

The pharmaceutical industry has developed drugs to help people lose weight. However, no drug has been discovered that allows individuals to eat all they desire and retain a sedentary lifestyle while simultaneously losing weight. Furthermore, the drug products available to the general public, whether by prescription or as over-the-counter preparations, are not free of risk. Known risks include valvular heart disease arising out of the use of the combination of fenfluramine and phentermine (Fen-Phen), and irregular heart beat (arrhythmia) that is associated with the use of phenylpropanolamine (PPA). These risks have resulted in bans on the use of these drugs in weight loss products and programs in some countries.

Health risks of anti-obesity preparations are not limited to prescription and/or over-the-counter medications. The use of ephedra in nutritional products employed for weight loss has been associated with arrhythmia and even sudden death in susceptible individuals.

Weight gain is caused by consuming more calories than the body requires for its basal metabolic functions and additional activities in which an individual is involved. The human body stores these excess calories as fatty deposits (lipids in adipose tissue) throughout the body, but is not able to readily access these fatty deposits to satisfy energy needs. To use these stored lipids as an energy source, the number of calories ingested must be less than the total energy expenditure of the body (basal metabolic rate plus activity level). Under hypocaloric conditions the body consumes fat as a source of fuel, but the switch to energy utilization of stored fat is not instantaneous. The body has feedback mechanisms that attempt to preserve existing lipid stores. Therefore, in the interim between the initial reduction in caloric intake and the conversion of lipids to energy, the body consumes lean body mass as a source of energy. Hepatic gluconeogenesis utilizes amino acids from muscle to generate glucose which the body uses as its preferred energy source. Hence, the body will consume some muscle tissue as its energy source during this period of conversion.

The use of lean body mass as an energy source is vitally important to normal physiology and maintenance of energy homeostasis. Under conditions of caloric restriction muscle tissue represents the primary energy source used to maintain the body's basal metabolic rate. However the reduction in lean body mass retards the loss of fat during periods of intentional caloric restriction intended to induce weight loss. Any weight lost as lean body mass represents weight that would otherwise have been lost as fat. The loss of lean body mass can also reduce muscle mass, which is often considered aesthetically and functionally undesirable.

Reduced caloric intake usually induces cravings for food that reduce adherence to weight loss regimens. These cravings are caused by both psychological and physiological mechanisms. For example, ingested carbohydrates are absorbed from the digestive tract into the bloodstream to increase blood glucose levels. In response to the increase in blood glucose, the pancreas releases insulin to aid in the transport of glucose into the cells of the body where glucose is employed as an energy source. However, if the amount of insulin released is greater than the amount of glucose present (which is often the case in overweight individuals), then the body reacts by signaling the brain to ingest more carbohydrates in order to balance the amount of insulin in the bloodstream. This insulin-induced craving for carbohydrates is very common during periods of caloric restriction.

Food cravings can also be attributed to a lack of specific food types. For instance, individuals who attempt to lose weight by eating a high protein, low fat diet often find themselves craving foods that contain fats. Although there are many "fat-free" foods available in commercially available products, they often lack the palatability provided by the presence of fat.

The use of soy protein in combination with soybean fibers, and optionally also in combination with other vitamins and minerals (such as iron, zinc, iodine, manganese, chromium, and selenium), has been described in U.S. Pat. No. 6,268,011.

The use of a chromium salt in nutritional products has been the subject of many patents, for instance, U.S. Pat. Nos. 4,954,492; 5,087,623; 5,175,156; 5,194,615; 6,251,888; 6,251,889; 6,323,192; 6,432,942; and 6,471,998. Some of these patents describe the use of a chromium salt, either alone or in combination with other ingredients, in lowering blood levels of lipids and/or controlling blood glucose levels. U.S. Pat. Nos. 5,087,624; 6,251,889; 6,323,192; 6,432,942; and 6,471,998 describe the use of chromium salts either alone or in combination with other materials for increasing lean body mass. In this latter context, the chromium salt is employed as an anabolic agent to increase muscle mass when taken while following a strength building exercise program. The use of chromium salts in dietary preparations is also described in U.S. Pat. Nos. 6,277,842; 6,399,089; and 6,413,545.

Layman et al. have recently noted that a higher protein diet improves utilization of body fat as an energy source, while reducing (but not eliminating) the loss of lean body mass. J. Nutr. 133:411-417, 2003. Layman has also noted that branched chain amino acids (BCAAs) such as leucine are linked to glucose homeostasis by enhancing recycling of glucose via the glucose-alanine cycle. The BCCAs also enhance translational regulation of muscle protein synthesis through the insulin signaling cascade. Increased leucine concentration is sensed by an element of the insulin-signaling pathway that triggers a phosphorylation cascade that stimulates the translational initiation factors eIF4 and $p70^{s6}K$. J. Nutr. 133:261S-267S, 2003. Although Layman found that reduced-calorie diets that included protein sources with high endogenous BCAA and leucine content (such as red meat, milk and cheese) did reduce loss of lean body mass, about 12-18% of total weight lost was lean body mass loss.

In spite of extensive prior research, there is still a need for a weight-loss product that helps promote a sensation of satiety to assist with a reduction in caloric intake, while substantially preserving lean body mass as weight loss occurs. Although many researchers have contributed to the complex body of knowledge about physiologic energy utilization under conditions of caloric restriction, existing nutritional supplements and regimens still result in an undesired loss of lean body mass.

SUMMARY

It has now been found possible to lose weight under conditions of caloric restriction (hypocaloric conditions) with a surprising preservation of lean body mass. This surprising result is achieved by providing an effective combination of soy protein, chromium and free leucine (which is referred to herein as "SCL"). The soy protein provides a balanced blend of amino acids for protein synthesis. The chromium enhances insulin sensitivity so that tissue uptake of glucose is promoted to spare utilization of muscle protein for this purpose. In addition, the free leucine is processed in skeletal muscle to provide gluconeogenic precursors to the liver for additional energy production. The free leucine also stimulates protein synthesis by enhancing translation initiation events and insulin-induced protein synthesis. Administering an adequately balanced combination of soy protein, chromium and free leucine has been found to be surprisingly effective in preserving lean body mass under conditions of caloric restriction and weight loss. This combination is also able to improve the subject's lipid profile.

The soy protein, chromium and free leucine may be administered in a dosage form (for example a drink or shake mix, or a combination of a shake mix, snack bar and supplement) that provides a daily dosage of at least 30 g of soy protein, at least 400 μg of chromium, and a sufficient amount of free leucine that the weight ratio of soy protein to free leucine is more than 10:1 for example more than 11:1, such as about 11.8:1 or 12.2:1 or 13:1. In other embodiments, the weight ratio of soy protein to free leucine is between 10:1 to 20:1, for example 10-15:1. In some examples, there is at least 2 g of free leucine. In particular examples, the soy protein, chromium and free leucine are present in the dosage form in an amount providing a daily dosage of 32-40 g of soy protein, 400-800 μg of chromium, and 2.25-4.0 g of free leucine, for example a daily dosage of about 35-39 g of soy protein, 600 μg of chromium, and 2.9 g of free leucine.

In certain examples, other forms of protein (such as whey protein) are substituted for the soy protein.

In some embodiments the dosage form further includes an amount of corosolic acid effective to inhibit the loss of lean body mass in the subject under conditions of caloric restriction. In particular examples the effective amount of corosolic acid is 0.25-1 mg of corosolic acid (for example about 0.3 mg), and the corosolic acid may be provided by banaba leaf extract. In even more particular embodiments the dosage form provides a daily dosage of 25-35 mg banaba leaf extract containing about 1% corosolic acid, 300-500 mg magnesium, 15-25 mg zinc, 50-150 μg vanadium, and 600-1000 mg taurine.

A particularly advantageous embodiment breaks the dosage form into multiple dosage forms, wherein the soy protein, chromium and free leucine are each distributed into more than one dosage form such as a drink mix, a consumable snack, and a supplement. For example, the dosage forms can include a drink mix that provides a daily dosage of 26-30 g soy protein, 100-300 μg chromium, and 2-3 g free leucine; a consumable snack (such as a snack bar) that provides a daily dosage of 6-10 g of soy protein and 0.25-1.0 g free leucine; and a supplement (such as an ingestible capsule or tablet) that provides a daily dosage of 300-500 μg chromium (for example distributed into three separate tablets that can be ingested at different times throughout the day to deliver equal separate doses of the chromium that aggregate to the daily dose). In some embodiments the dosage form also includes a tea preparation, such as a tea bag or tea leaves in a prepackaged unit, which can be made into a drink that provides a daily dosage of 700-900 mg taurine (for example in a single or multiple servings).

In particular examples, the dosage forms are administered in a pattern consistent with social norms for daily nutritional intake. For example, the drink mix is divided into two dosage units that substantially equally divide the daily dosage between the two units, for example two drink (such as shake) servings per day that substitute for two different meals (such as breakfast and lunch, or breakfast and dinner, or any other combination of two meals). In certain specific examples, the dosage form is made up of three component dosage forms, such as a drink mix administered in a liquid base twice a day (abbreviated "bid"), a snack consumed once a day, and a supplement consumed once, twice or three times a day, wherein the dosages provided by the dosage form are distributed as follows and provide the indicated daily totals:

|  | Per serving | | | |
|---|---|---|---|---|
|  | Drink Mix | Snack | Supplement | Daily Total |
| Soy protein (g) | 13-15 | 6-10 |  | 32-40 |
| Chromium (μg) | 50-150 |  | 300-500 | 400-800 |
| Banaba leaf extract (mg) |  |  | 25-35 | 25-35 |
| Magnesium (mg) | 100-175 |  | 100-150 | 300-500 |
| Zinc (mg) | 3-7 |  | 9-11 | 15-25 |
| Vanadium (μg) |  |  | 50-150 | 50-150 |
| Free Leucine (g) | 1-1.5 | 0.25-1 |  | 2.25-4 | for example approximately

|  | Per serving | | | |
|---|---|---|---|---|
|  | Drink Mix (bid) | Snack | Supplement | Daily Total |
| Soy protein (g) | 14.2 | 8.4 |  | 36.8 |
| Chromium (μg) | 100 |  | 400 | 600 |
| Banaba leaf extract (mg) |  |  | 32 | 32 |
| Magnesium (mg) | 140 |  | 120 | 400 |
| Zinc (mg) | 5.25 |  | 9.75 | 20.25 |
| Vanadium (μg) |  |  | 100 | 100 |
| Free Leucine (g) | 1.2 | 0.5 |  | 2.9 |

Since the drink mix is consumed twice a day in this example, the drink mix provides twice the daily dosage listed under the "Drink Mix" heading in the table (about 28.4 g of soy protein, about 200 μg of chromium, about 280 mg of magnesium, about 10.5 mg of zinc, and about 2.4 g of free leucine). The Supplement dosages are set forth above as a unit dose, but they are preferably split into multiple dosage forms (such as three tablets that can be taken substantially simultaneously or at different times throughout the day, such as at morning, noon and night). When the Supplement is administered in three tablets, each of the tablets provides about one-third of the amounts listed in the Supplement column (about 133 µg chromium, 10.6 mg banaba leaf extract, 40 mg magnesium, 3.25 mg zinc, and 33 µg vanadium).

In yet other embodiments, the dosage form further includes a tea preparation component that delivers a single daily dosage of about 700-900 mg taurine, for example 800 mg taurine, so that the dosage form delivers substantially the following daily total dosages in the following forms, the drink mix dosage is administered twice a day (for example at breakfast and lunch or breakfast and dinner), the supplement dosage is delivered in either a single dosage (for example in the morning), or divided into three dosages (for example morning, noon and evening), and the snack and tea daily dosages are provided in a single serving of each (for example in mid-afternoon):

|  | Per serving | | | | |
| --- | --- | --- | --- | --- | --- |
|  | Drink Mix (bid) | Snack | Supple-ment | Tea | Daily Total |
| Soy protein (g) | 13-15 | 6-10 |  |  | 32-40 |
| Chromium (µg) | 50-150 |  | 300-500 |  | 400-800 |
| Banaba leaf extract (mg) |  |  | 25-35 |  | 25-35 |
| Magnesium (mg) | 100-175 |  | 100-150 |  | 300-500 |
| Zinc (mg) | 3-7 |  | 9-11 |  | 15-25 |
| Vanadium (µg) |  |  | 50-150 |  | 50-150 |
| Taurine (mg) |  |  |  | 700-900 | 700-900 |
| Free Leucine (g) | 1-1.5 | 0.25-1 |  |  | 2.25-4 | such as

|  | Per serving | | | | |
| --- | --- | --- | --- | --- | --- |
|  | Drink Mix (bid) | Snack | Supple-ment | Tea | Daily Total |
| Soy protein (g) | 14.2 | 8.4 |  |  | 36.8 |
| Chromium (µg) | 100 |  | 400 |  | 600 |
| Banaba leaf extract (mg) |  |  | 32 |  | 32 |
| Magnesium (mg) | 140 |  | 120 |  | 400 |
| Zinc (mg) | 5.25 |  | 9.75 |  | 20.25 |
| Vanadium (µg) |  |  | 100 |  | 100 |
| Taurine (mg) |  |  |  | 800 | 800 |
| Free Leucine (g) | 1.2 | 0.5 |  |  | 2.9 |

Of course the daily dosages can be delivered in any combination of servings, such as divided between multiple servings of the drink mix, snack, supplement and tea component dosage forms.

Also disclosed herein is a method of promoting weight loss in a subject while substantially or even completely preserving lean body mass. The method includes administering a daily dosage of at least 30 g of soy protein, at least 400 µg of chromium, and a sufficient amount of free leucine that the weight ratio of soy protein to free leucine is more than 10:1, for example 10-20:1, such as 10-15:1. In particular embodiments the ratio is more than 11:1, such as about 11.8:1, 12.2:1 or 13:1, while sufficiently restricting caloric intake of the subject to induce weight loss. In some examples, there is at least 2 g of free leucine. An advantage of this method is that weight loss can surprisingly occur with substantially no loss of lean body mass, and lean body mass can in some examples even be completely preserved (including instances in which lean body mass does not change or even increases).

In certain examples, a daily dosage is delivered of 32-40 g soy protein, 400-800 µg chromium, and 2.25-4.0 g free leucine, for example a daily dosage of about 35-39 g soy protein (such as about 36.8 g), about 600 µg chromium, and about 2.9 g free leucine. Any or all of the dosages can be divided into multiple dosage components, however it has been found particularly advantageous for the dosage of soy protein and free leucine to be divided into one snack and two servings of the drink mix wherein the drink mix is dispensed as a beverage after the powdered mix is dissolved or otherwise suspended in a liquid base (such as water or reduced fat/low fat/skim milk). In particular embodiments the drink mix is delivered as a "shake" that provides a thickened consistency to a liquid in which it is dispensed (for example thickening the consistency of a milk base in which it is delivered).

In other examples the method also includes administering an amount of corosolic acid effective to inhibit the loss of lean body mass in the subject while sufficiently restricting caloric intake of the subject to induce weight loss. In disclosed embodiments the amount of administered corosolic acid is 0.25-1 mg corosolic acid, for example about 0.3 mg corosolic acid, which can be administered in banaba leaf extract (a source of corosolic acid). In other examples the method further comprises administering a daily dosage of 10-35 mg banaba leaf extract (as the source of corosolic acid, about 1-3% by weight of the extract), 300-500 mg magnesium, 15-25 mg zinc, 50-150 µg vanadium, and 600-1000 mg taurine.

In certain embodiments of the method, the soy protein, chromium and free leucine are each distributed into more than one dosage form. Administering these different dosage forms at different times throughout the day helps maintain their physiological availability in a more sustained fashion. In addition the distribution of dosages throughout the day can better mimic food intake according to social norms in which subjects traditionally consume food in three meals throughout the day (such as breakfast, lunch and dinner). For example, the soy protein is delivered in two different delivery vehicles (such as a powdered beverage mix and a snack bar), the chromium is delivered in two different vehicles (such as the powdered beverage mix and a supplement), and the free leucine dosage is divided between the powdered drink mix and the snack bar. The method can also include separately administering a tea preparation, for example to provide a dosage of 700-900 mg taurine.

A particular example of the method includes administering a daily dosage in a beverage (as from a powdered beverage mix) of 26-30 g soy protein, 100-300 µg chromium, and 2-3 g free leucine; administering the consumable snack that provides a daily dosage of 6-10 g soy protein and 0.25-1 g free leucine; and administering the supplement that provides a daily dosage of 300-500 µg chromium. In particularly disclosed embodiments the soy protein is delivered in divided dosages by administering two substantially equal dosages of the beverage mix per day (where the mix is delivered in a liquid base) as a substitute for two different meals on the same day, the consumable snack is eaten once per day in between meals (for example in mid-afternoon between lunch and dinner), and the supplement is ingested in three separate dosages at different times of the day (for example morning, noon and evening). In some embodiments a brewed drink (such as tea) is also administered, for example as a source of taurine.

The method may also include providing no more than one full meal a day, although supplemental food may also be consumed. The additional food can be selected to maintain a particular daily consumption of calories, with the goal of maintaining the subject in a condition of a caloric deficit with respect to calories consumed and energy expended. Providing a meal and/or supplemental food includes (without limitation) either advising consumption of it or actually dispensing it (as in a prepackaged form). A meal or the supplemental food could be, for example, a dinner that does not include any of the beverage, snack, supplement or tea. In some embodiments supplemental food may be administered by itself or together with the snack depending on the caloric requirements of the individual.

Meals and supplemental foods are designed to be well-balanced and include nutritious food choices from a variety of food groups such as meat, fruit, vegetables, breads and cereals and fats. When the meals and/or supplemental foods are consumed with certain embodiments of the method (such as the powdered beverage mix and snack) as part of a total weight loss program, they may provide a macronutrient balanced diet with approximately 40%-45% of calories coming from carbohydrate, 25-30% of calories coming from protein and 25-30% of calories from fat. The source of carbohydrates provided in the meals and snacks is primarily from complex carbohydrates (whole grain breads and starches, fresh fruits and vegetables) which are good sources of dietary fiber and tend to have a low glycemic index. Protein food choices are from leaner cuts of meats, chicken, turkey and fish and the fat content in the meals tends to come from monounsaturated fats (ie. olive and canola oils) so as to limit intakes of saturated and trans fats whenever possible. Meals and supplemental food are incorporated into a range of calorie levels (1200, 1500, 1800 and 2100) and several variations including no dairy, no red meat and lacto-ovo vegetarian meal plans.

The method can also include reducing hyperlipidemia, for example by reducing one or more of total cholesterol, LDL cholesterol, and the total cholesterol:HDL ratio, by administering any of the soy protein, chromium and free leucine combinations, or by following the methods described above for promoting weight loss.

The soy protein, chromium and free leucine compositions can be included in a weight loss kit that includes the dosage forms described above, in combination with instructions for its use to lose weight while preserving lean body mass. Particular embodiments of the kit provide instructions for consuming the components of the kit (such as the powder, snack, tea and supplement) in a manner that provides the desired dosages of the various components in a manner that enhances their effect of losing weight while preserving lean body mass.

DETAILED DESCRIPTION

Abbreviations

BID: Twice a day.

SCL: Soy/Chromium/Leucine (a composition that contains soy protein, chromium and free leucine).

Explanation of Terms

"Administering" a dosage or dosage form includes self-administration by the subject, administration by another to the subject, and providing advice for administration to the subject (as in instructions provided in a tangible medium, such as printed instructions or advice on a computer readable medium). Administration by another to the subject can include, for example, administration by a physician, nurse or other health care provider or dietary consultant. Administration also includes providing an end product (such as a mixed beverage) that is consumed, or precursors that contain the end product (such as a powdered mix to be dispensed in a beverage) that another (such as the subject) may prepare for consumption.

Amounts expressed herein as percentages are percentages by weight unless indicated otherwise.

As used herein, a "condition of caloric restriction" refers to a condition in which a subject is following a calorically restricted diet and on average consumes fewer calories than are expended in a relevant period, such as a day, a week, a month, or longer. In certain examples, depending on the activity of the subject, the subject consumes less than or equal to about 2,100 total calories per day (on average), for example, a diet of from about 1,800 to about 2,100 calories per day, or in other cases a diet of from about 1,500 to about 1,800 calories per day, or in other cases a diet of from about 1,200 to about 1,500 calories per day. In still other cases an individual follows a diet of less than 1,200 calories per day. In some examples, an individual remains under conditions of caloric restriction for from about a day to about a year or longer, for example, for about one week, for about one month, for about 8 weeks, for about 12 weeks, or for about one year.

Ingredients can be "distributed into more than one dosage form," meaning that one ingredient (such as soy protein) may be administered in different dosage forms (for example in both a shake mix and snack).

A "dosage form" comprises any preparation, or combination of preparations, that provides a desired dosage. Hence a dosage form can include a single composition (such as a powdered beverage mix or other ingestible preparation) or a combination of several different compositions (such as a powdered beverage mix, a snack and a supplement). A dosage form can "provide a daily dosage" in either a single unit dosage form (such as a tablet or a liquid beverage in which the powder mix is dispensed) or in multiple dosages taken at different times throughout a day. Hence a dosage form that includes multiple sub-dosage forms can provide the total daily dosage administered at different times during a day (for example at breakfast and lunch), and in different forms (for example as a liquid beverage and a chewable snack bar). A particular example of a dosage form is an artificial preparation that includes a pharmaceutical carrier. A further distinction can be drawn between an exogenous preparation and a food preparation, wherein an exogenous preparation is in addition to consumed conventional food.

"Free leucine" refers to leucine in its amino acid form, and not contained in proteins, as it would be found in foods. The free leucine can, for example, be a single amino acid of leucine in the form of the free base or as a salt of leucine (such as but not limited to leucine hydrochloride), or an ester of leucine (such as but not limited to a methyl- or ethyl ester), or a chelate of leucine such as but not limited to a metal (such as copper chelate). The preferred form of the amino acid is L-leucine, which is the preferred biologically active form of the amino acid. The free leucine can also include analogs, variants, derivatives and precursors of leucine that provide an equivalent effect. The amounts of free leucine in the product formulations contained herein are expressed as the free base, without any accompanying counterion.

"Hyperlipidemia" refers to an elevation of lipids (fats) in the bloodstream that predispose a subject to the development of atherosclerosis. These lipids include cholesterol, cholesterol esters, phospholipids and triglycerides. They are transported in the blood as part of large molecules called lipoproteins. Examples of hyperlipidemic levels of certain lipid components in the blood include an LDL (low density lipoprotein) of more than 130 mg/dl, a total cholesterol of greater than 200 mg/dl, or triglyceride levels of more than 150 mg/dl.

"Dyslipidemia" refers to hyperlipidemia or any other dysregulation of the lipid profile, for example undesired levels of HDL or total cholesterol/HDL ratios.

It is generally preferred that HDL cholesterol, which is believed to provide a protective function, not be less than 40 mg/dl in men or 50 mg/dl in women. An additional factor to consider is the total cholesterol/HDL ratio. A typically accepted goal is to keep this ratio below 5:1; the optimum ratio is below 3.5:1.

A method of treating hyperlipidemia or other abnormal lipid levels can improve levels of one or more of these blood levels, to return them towards or to within the desired ranges. For example with the methods disclosed herein, the lipid levels can be moved from a higher risk range to a lower risk range (for example from high to borderline, or borderline to desirable).

Desirable: TC<150 mg/dL, HDL>50 mg/dL, LDL<130 mg/dL

Borderline: TC 200-239, HDL>40-50 mg/dL, LDL 131-159 mg/dL

High: LDL>160 or TC>240 mg/dL or HDL<40 mg/dL.

As used herein, the terms "individual" or "subject" refer to an animal, such as a mammal, for example a human.

A subject's "lean body mass" is the mass of the individual that is muscle, vital organ, bone and connective tissue. Under conditions of caloric restriction an individual loses body weight in the form of both lean body mass and fat. Loss of lean body mass is "inhibited" when, under conditions of caloric restriction, the relative loss of lean body mass is less than would be expected based on the difference between the number of calories ingested and expended. One measure of the inhibition of loss of lean body mass is a reduction in the percent of lean body mass lost as a percentage of total body mass lost. Lean body mass is "substantially preserved" when lean body mass loss is partially or completely inhibited. In particular examples disclosed herein, lean body mass loss is completely inhibited, so that there is no loss of lean body mass as measured herein. Loss of lean body mass is estimated by determining body fat percentage using calipers.

"Metabolic Syndrome" is a condition indicated by a concurrence of disturbed glucose and insulin metabolism, overweight and abdominal fat distribution, mild dyslipidemia, and hypertension, and is associated with subsequent development of type 2 diabetes mellitus and cardiovascular disease (CVD). As used herein, a subject having Metabolic Syndrome has at least three of the following clinical features: a waist circumference greater than about 102 cm in men and about 88 cm in women; serum triglycerides level of at least about 150 mg/dL (1.69 mmol/L); high-density lipoprotein cholesterol level of less than about 40 mg/dL (1.04 mmol/L) in men and about 50 mg/dL (1.29 mmol/L) in women; blood pressure of at least about 130/85 mm Hg; or serum glucose level of at least about 110 mg/dL (6.1 mmol/L). This definition corresponds to the recent definition noted in the Journal of the American Medical Association. Ford et al, JAMA, 287:356-359, 2002.

A "shake mix" or "drink mix" or "beverage mix" refers to a mixture, such as a powdered mixture, that is suitable for mixing in a liquid base (such as water or milk) to provide a beverage in which the mixture is dispensed to a subject. The shake mixture increases the thickness of the liquid base.

A "snack" refers to an edible solid having at least some organoleptic properties consistent with food. Examples of a snack include a snack bar (similar in appearance and mouth feel to a chewable candy bar), and a solid snack (more similar in appearance and mouth feel to a hard candy).

A "supplement" refers to a non-food form of dosage administration other than the liquid beverage or a solid snack. An example of a supplement is a pharmaceutical preparation (such as a tablet, enteral liquid, parenteral liquid, capsule, intranasal liquid or other form). In a particular disclosed example the supplement is a pharmaceutical preparation, in particular a tablet or capsule.

"Supplemental food" refers to food that is provided in addition to the drink mixture, snack, supplement and tea.

In certain embodiments, the shake mix, snack and supplement are an exogenous preparation that is administered or consumed in addition to food preparations such as the prescribed diet and supplemental food.

The other above noted criteria are evaluated by any reliable means, such as those conventionally used in medical examinations. Serum triglycerides, glucose levels and high-density lipoprotein cholesterol levels are measured, for example by standard blood chemistry panels. Blood pressure is measured for example by a sphygmomanometer.

Example 1

Starting Materials

Soy protein/chromium/free leucine (SCL) compositions for inhibiting loss of the lean body mass under conditions of caloric restriction are disclosed herein. Such compositions include soy protein and chromium and free leucine in amounts that are effective to inhibit or even avoid the loss of lean body mass in an individual under conditions of caloric restriction.

Soy protein, as used herein, refers to the protein component obtained from the soybean plant and/or from concentrated sources such as soy protein isolates. In some cases the soy protein is isolated from the soybean by methods well known in the art. For example, a concentrated soy protein fraction is prepared from cleaned, dehulled soybeans by removing a majority of the non-protein components so that the isolated product contains at least about 80% protein by total weight (including moisture content). The soy protein isolate is prepared through a series of steps in which the soybean protein portion is separated from most of the remainder of the soybean. In particular examples, bland tasting soy protein isolate materials are used. Further, although genetically modified soy (GM soy) protein is used in some cases, non-genetically modified soy (Non-GM soy) protein may also be used. Such soy protein isolates are available from a variety of companies such as Protein Technologies, Inc. Soy protein isolate refers to the material isolated from the soybean plant, a portion of which is soy protein. In certain examples disclosed herein, a soy protein isolate contains about 85% soy protein. In such an example, a dose of 14.2 g of soy protein is contained in 16.7 g of soy protein isolate (0.85×16.7=14.2).

As used herein, chromium refers to chromium in a biologically acceptable salt or chelate of chromium. It is provided in any bioactive and physiologically acceptable form. Though the chromium is provided in many forms, when referring to an amount of chromium herein it is meant the amount of actual chromium in the biologically acceptable salt or chelate (for example, 100 µg of chromium is provided by about 1.0 mg of the biologically acceptable chelate chromium nicotinate). In some cases the chromium is in the form of a chromium salt, such as chromium chloride, while in other cases it is in the form of a chromium chelate, such as chromium nicotinate (including mononicotinate, dinicotinate, trinicotinate, and polynicotinate), chromium picolinate (including monopicolinate, dipicolinate, and tripicolinate), protein chelates, and chelates of any bioavailable organic acid (such as amino acids), or compositions or combinations thereof, such as a composition of chromium mononicotinate, dinicotinate, trinicotinate, and polynicotinate or monopicolinate, dipicolinate, and tripicolinate. In particular examples chromium is provided in the form of chromium nicotinate or picolinate. An effective amount of chromium for use in inhibiting the loss of lean body mass is from at least about 50 or 100 µg per serving or dose and ranges to about 1 milligram (mg) per serving or dose or daily total dose. In particular examples an effective amount of chromium is from about 100 µg, to about 200, 400 or 600 µg.

Amino acids are the constituent building blocks of proteins that are covalently bound together by peptide bonds. The amino acids are grouped into different structural and functional categories. One such category is the "branched chain amino acids" (BCAAs) which are leucine, valine and isoleucine. Individual or isolated amino acids are readily commercially available from a variety of sources. The L-amino acids are the biologically active forms, and are the type typically administered in supplement preparations.

Corosolic acid (2-alpha-3-beta-dihydroxy-12-ursen-28-oic acid; 3-alpha, 3-beta-di-hydroxyursolic acid) refers to a triterpene compound that can be extracted from the leaves of the plant *Lagerstroemia speciosa* (banaba leaf) and *Punica granatum* and also is known as colosolic acid and botanical insulin. As used herein corosolic acid also refers to equivalent effective amounts of pharmaceutically acceptable salts, analogs, derivatives, isomers, and metabolites of corosolic acid such as, methyl and glucopranosyl esters (at the carbonyl group), and methyl, acetyl, or cinnamoyl substitutions (at one or more hydroxyl group) that retain the desired biological effect of corosolic acid.

In some cases the disclosed compositions include other ingredients for added nutrition, preservation, or flavor, such as fructose, high oleic sunflower oil powder, acacia gum, canola oil, inulin, short chain fructooligosaccharides, dicalcium phosphate, silicon dioxide, sodium citrate, potassium chloride, magnesium oxide, lecithin, whey protein isolate, rice protein concentrate, cocoa powder, guar gum, flavoring, sweeteners (for example honey), and vitamin and mineral premixes. Vitamin premixes include, for example, premixes of ascorbic acid, mixed tocopherol concentrate, d-alpha tocopheryl acetate, vitamin A palmitate, vitamin B 12, vitamin D3, pyridoxine hydrochloride, riboflavin, thiamine mononitrate, niacinamide, calcium pantothenate, folic acid, and biotin. Mineral premixes include, for example, ferrous fumarate, potassium iodide, molybdenum yeast, selenium yeast, zinc oxide, copper gluconate, manganese sulfate, and potassium iodide.

In specific examples where vitamin and mineral premixes are included in a combined soy protein/chromium/free leucine composition (such as a shake mix), the weight of the soy protein is from about 10% to about 50% of the total weight of the composition, for example, the soy protein is from about 20-40% or about 25-35% of the total weight of the composition; the weight of the chromium in the bioactive form provided (such as chromium nicotinate) is from about 0.0005% to about 0.10% of the total weight of the composition, for example the weight of the chromium is from 0.002% to about 0.01% of the total weight of the composition or, in an even more specific example, from about 0.002% to about 0.003% of the total weight of the composition; and the weight of the free leucine is from about 1% to about 10% of the total weight of the composition, for example, the weight of the free leucine is from about 1-5% or about 1-3% of the weight of the total composition. In certain instances the other ingredients are also used in certain relative amounts. In certain cases the weight of fructose is about 20% to about 35% of the total weight of the composition, for example the weight of fructose is about 30% to about 33% of the total weight of the composition; the weight of high oleic sunflower oil powder is about 5% to about 7% of the total weight of the composition, for example about 6% to about 7% of the total weight of the composition; the weight of acacia gum is about 8% to about 16% of the total weight of the composition, for example about 10-15% of the total weight of the composition; the weight of canola oil is about 0.4% to about 4% of the total weight of the composition, for example, about 0.6% of the total weight of the composition; the weight of short chain fructooligosaccharides is about 3% to about 5% of the total weight of the composition, for example about 4% of the total weight of the composition; the weight of guar gum is about 0.3% to about 0.5% of the total weight of the composition; dicalcium phosphate is about 1-3%, for example about 2%; the weight of silicon dioxide is about 0.5-2%, for example about 1%; the amount of sodium citrate is 1-2%, for example about 1.2%; the amount of potassium chloride is about 0.5-2%, for example about 1%; the amount of flavoring (such as vanilla flavor) is about 1-3%, for example about 2%; the amount of lecithin (such as soy lecithin) is about 0.5-2%, for example about 1%; the amount of whey protein isolate is 0.5-2%, for example about 0.9%; the amount of the rice protein concentrate is about 0.1-1%, for example about 0.4%, and the amount of magnesium oxide is about 0.25-2%, for example about 0.6% by weight of the composition. The composition may also contain, for example about 0.05-0.15% of inulin, such as about 0.1% of inulin.

In some examples the powdered beverage mix includes a separate or included vitamin mix component, which is about 0.05% to about 2% of the total weight of the composition, for example, the weight of vitamin mix is about 0.15% to about 0.2% of the total weight of the powdered premix. The vitamin mix component may include, for example, the following in amounts of greater than zero but less than 0.1% of each of ascorbic acid, mixed tocopherol concentrate, d-alpha tocopheryl acetate, vitamin A (as in vitamin A palmitate), niacinamide, pantothenic acid (for example in the form of calcium pantothenate), vitamin B12, vitamin D3, pyridoxine (as in the hydrochloride salt), riboflavin, thiamine (as in the mononitrate form), folic acid, and biotin. In disclosed embodiments the vitamin mix component comprises less than 0.2% of the total weight of the powdered beverage mix.

The powdered beverage mix may also include a mineral mix component that is separate from or included in the powdered mix, and which comprises less then 1% by weight of the total beverage mix, for example less than 0.5% by weight, such as about 0.1% by weight. In particular examples, the mineral mix component includes selenium (for example as selenium yeast), molybdenum (for example as molybdenum yeast), zinc (for example as the oxide), copper (for example as the gluconate), manganese (for example as the sulfate), chromium (for example as the nicotinate), potassium (for example as the iodide), and iron (for example as ferrous fumarate). Additional nutritional supplements, preservatives, and flavorings are included in some instances. One of ordinary skill in the art would be able to determine appropriate combinations of these ingredients and others for adding nutrition to the composition, preserving the composition from spoilage, and/or adding flavor to it.

As already noted, the soy protein/chromium/free leucine composition is in some examples a dry drink powder. For example, each component of the composition is mixed together into a powder. In one specific case such a powder is made by combining the liquid ingredients (lecithin, canola oil and mixed tocopherol concentrate) in a vessel and mixing these ingredients to form a homogenous mixture. In a separate vessel all the dry ingredients including the soy protein, chromium and free leucine are combined (except silicon dioxide and a portion of high oleic sunflower oil powder). The vessel may be a blending device, or the dry ingredients can be transferred to an appropriate blending device, preferably one equipped with a chopping device. The dry ingredients are then mixed thoroughly.

While mixing the dry ingredients, the liquid ingredients are introduced onto the well-blended dry ingredients in an even and consistent fashion, preferably with a spraying device. After the addition of the liquid ingredients, the mixture is mixed (such as by tumbling) and chopped until it is well blended. The remainder of the high oleic sunflower oil powder and silicon dioxide is then added to the mixture and the entire mixture is blended until these ingredients are also well blended into the mixture, which forms a dry powder.

The powdered mix may be administered as a beverage in a liquid base. For example, in some instances a dry drink powder is mixed with a liquid such as water (for example purified water), milk (for example non-fat milk), or juice and agitated to mix the liquid and the powder to create a shake drink having a thicker consistency than the original liquid base. This mixing is sometimes performed before the composition is packaged, and sometimes is performed by the consumer of the composition.

In an example in which 1 cup of non-fat milk (245 g) is mixed with the shake powder (48-50 g), certain specific examples of the relative amounts of the components of the shake drink, as expressed in weight of the ingredient to the total weight of the shake drink are from about 60% to about 95% liquid, such as non-fat milk, for example from about 75% to 85% liquid, from about 2% to about 30% soy protein, for example from about 2% to about 15% soy protein (preferably 5-6%) from about 0.2 to about 1% of free leucine (not present in proteins), from about 0% to about 5% other proteins, such as whey protein or rice protein or combinations thereof, for example, from about 0.05% to about 0.2% other protein, from about 2% to about 12% carbohydrates, for example, from about 6% to about 10% carbohydrates, from about 0.5% to about 5% fats (lipids), for example, from about 1% to about 3% fats, from about 1% to about 10% fiber, for example, from about 1% to about 5% fiber, and a trace percentage of chromium, for example, from about 80 µg to about 200 µg, and vitamin premix, mineral premix, and other ingredients as desired.

A dietary program that includes the shake mix and supplements is designed to maintain protein intake at about 30% of total calories consumed, total carbohydrate content of the program not greater than 50% (and preferably closer to 40-45%) of total calories consumed, while fat intake does not exceed 30% of total calories or go below 20% of calories consumed. In disclosed embodiments, the shake composition itself provides about 35% calories from protein, 50% calories from carbohydrate and 15% calories from fat. The disclosed snack bars provide roughly 32% calories from protein, 48% calories from carbohydrate and 20% calories from fat.

The administered compositions can be made to have any desired amount of calories. In some examples, the soy protein/chromium/free leucine compositions contain from about 100 to about 200 calories as the powder and from about 250 to about 300 calories when mixed with non-fat milk. In particular instances the compositions contain no more than about 200 calories as the powder, or no more than 350 calories when mixed with non-fat milk or another vehicle such as soy milk. The caloric content of the composition that is administered is deducted from the total number of calories consumed per day to arrive at a total caloric intake that will achieve the desired caloric restriction. The caloric content of the snack bars may be, for example, 100-150 calories, such as 130 calories.

Example 2

Methods of Promoting Weight Loss

This Example discloses general methods of promoting body weight loss and/or improvements in lipid profile that include consuming a combination of soy protein, chromium and free leucine under conditions of caloric restriction in amounts sufficient to inhibit the loss of lean body mass. As used herein, a method of losing weight refers to a conscious effort to reduce body weight, whether measured in body weight or another measure of weight loss (for example, body mass index or BMI). In some cases a soy protein/chromium/free leucine combination is consumed as a combined soy protein/chromium/free leucine combination composition, as discussed above. In other cases the soy protein, free leucine and the chromium are consumed separately. In some instances, the method further includes instruction regarding a calorically restricted diet. In certain embodiments the method promotes weight loss in a subject having the Metabolic Syndrome.

Methods are also disclosed for treating an overweight subject by selecting an overweight subject and administering to the subject (for example, instructing or otherwise causing the subject to consume) the combination of soy protein, free leucine and chromium in amounts effective to inhibit or even avoid the subject's loss of lean muscle mass under conditions of caloric restriction. In some cases the combination is administered as the disclosed soy protein/chromium/free leucine powdered composition. In other cases the soy protein, chromium and free leucine are administered separately. In other embodiments the combination is distributed between the powdered composition and other preparations, such as a snack preparation and/or supplements.

Selecting an overweight subject includes selecting an individual having an excess of body weight that puts the subject at risk for complications associated with being overweight. For example, weight-related complications include hypertension, dyslipidemia, type-2 diabetes (non-insulin dependent diabetes mellitus or NIDDM), coronary heart disease, stroke, gallbladder diseases, osteoarthritis, sleep apnea, and respiratory problems. Typically, being overweight refers to having an excess of body weight compared to set standards. A generally accepted standard for determining whether a human is overweight is BMI, which is calculated as weight in kilograms (kg) divided by height in meters squared ($m^2$). Generally an individual having a body mass index (BMI) of at least 25 is considered overweight. However, BMI is not always an accurate measurement of whether an individual is overweight for the purposes of determining whether the individual's weight constitutes a health risk. For example, a muscular athlete may have a high BMI because of the large amount of weight the individual carries as muscle, in the absence of health risks generally associated with being overweight. Other indicators such as percentage body fat are also used in making this determination. Additionally, the location of an individual's body fat is also relevant. Body fat concentrated in the abdominal region and/or around the hips is associated with a higher risk for most overweight associated complications than body fat concentrated in other areas, such as the legs. One of ordinary skill in the art would be able to determine whether a person is overweight in this medically relevant sense.

An obese individual is a particular example of an overweight person who may be treated with the methods disclosed herein. As used herein the term obese refers to an individual having an abnormally high proportion of body fat. Typically an individual with a BMI of 30 or higher would be considered obese.

In certain cases selecting an overweight subject further includes selecting a subject having Metabolic Syndrome, for example by testing the subject for the clinical features of Metabolic Syndrome.

In some cases the soy protein/chromium/free leucine combination is consumed orally in any ingestible form. In some instances the soy protein/chromium/free leucine combination is consumed in a composition described elsewhere herein. In some instances the soy protein/chromium/free leucine composition is consumed as a dry powder, in others as a shake drink, and in still others in bar form. In some examples the soy protein/chromium/free leucine combination is consumed using enteral delivery methods, for example through a nasogastric tube or percutaneous endoscopic gastrostomy (PEG) tube.

In some examples at least some of the components of the combination are consumed separately. For example at least some of the chromium may be separately consumed orally or enterally in any ingestible form, such as capsules (hard or soft), tablets, elixirs, powders, granules, suspensions in water or non-aqueous media, or as an additive to food or beverages. In some cases the chromium is mixed with a pharmaceutical carrier (conventional tableting ingredients such as corn starch, lactose, maltodextrin, sucrose, sorbitol, talc, stearic acid, magnesium stearate, dicalcium phosphate or gums) and/or other pharmaceutical diluents, such as water, to form a solid preformulation composition containing a substantially homogenous mixture of the composition, or a non-toxic pharmaceutically acceptable salt thereof. When referring to the preformulation compositions as substantially homogenous, it is meant that the active ingredients are dispersed evenly throughout the composition so that the composition may readily be subdivided into equally effective unit dosage forms such as capsules, pills, and tablets. In other cases the chromium is consumed in liquid preparations for oral administration, such as solutions, syrups, or suspensions.

The disclosed methods include administering to a subject the disclosed soy protein/chromium/free leucine combinations or compositions for a length of time sufficient to have the desired effect. In certain cases the soy protein/chromium/free leucine combinations are consumed daily for a week or more, for example for up to a year or more. In particular examples, the combinations are consumed for a period of from about 8 weeks to about 12 weeks, for example, either 8 weeks or 12 weeks. In other cases the combinations are consumed for a period of about five days or more.

In some situations an individual or subject is instructed regarding a calorically restricted diet. For example the subject may be orally instructed concerning the need to consume fewer calories than the subject expends to achieve a condition of caloric restriction. In other instances instructions are provided in written form. In certain cases the subject is also advised regarding how to determine the caloric content of foods by reading the information labeling on food products or by accessing other data regarding the caloric content of various foods. In some instances, the subject is instructed concerning the effects of portion or serving sizes of various foods on weight loss. In some instances the subject is also instructed concerning obtaining adequate nutrition during periods of caloric restriction as well as warning signs of improper or dangerous caloric restriction and nutritional deficiencies.

In some examples the individual or subject is instructed regarding participation in exercise with either oral or written instructions to participate in an exercise such as walking at least one mile or for at least 30 minutes each of at least five days a week, or exercise with a similar or higher level of exertion. Still other embodiments include performance of such exercise by the subject, or an absence of exercise by the subject.

Some embodiments of the methods further include consuming corosolic acid, and optionally one or more of magnesium, zinc, taurine, and vanadium. These agents may, for example, be components of the soy protein/chromium/free leucine powdered composition, or they may be consumed separately from the composition, for example in a separate nutritional supplement or supplements (such as tablets).

If the nutritional supplement is consumed separately from the soy protein/chromium/free leucine powdered composition, the nutritional supplement is consumed at any time or times of the day. In certain embodiments the nutritional supplement is consumed at or near the time of one or more meals in a day, such as the largest meal of the day, for example within half an hour of the meal or during the meal. In some embodiments, the nutritional supplement is consumed in two or more doses, for example at or near the time of the two largest meals of the day, or at or near the time of each of three meals of the day (breakfast, lunch and dinner).

In certain embodiments where the soy protein/chromium/free leucine combination and the corosolic acid are administered, subjects are not instructed regarding a calorically restricted diet and are not required to follow any particular diet, and/or do not consciously follow a calorically restricted diet.

Example 3

Kits

Components of the dietary regimen may be provided in kits, such as packages that may or may not include instructions regarding a calorically restricted diet; instructions to follow or not follow any particular diet; and/or instructions to consciously follow or not consciously follow a calorically restricted diet. In other embodiments, subjects are instructed to follow or are not instructed to follow a prescribed exercise regimen.

These kits can include the compositions described elsewhere in this specification. For example, the kit can contain the powdered drink mix, a snack bar, the tea mix, and the supplement.

The instructions provided with the kit are in a fixed form, such as written or recorded onto an audiocassette, videocassette, compact disc, or digital videodisc. The instructions instruct an individual about amounts of the kit components to consume in order to inhibit the loss of lean body mass while dieting, or to achieve an improvement in blood lipid levels.

In some cases the kits contain a composition of soy protein/chromium/free leucine, such as a shake drink comprising soy protein, chromium, and free leucine. In other cases the composition is provided in the form of a dry drink powder, with instructions to mix it in a liquid delivery vehicle. In some instances the composition is provided in bulk form, with more than one serving per container. In such cases the instructions inform an individual to consume a certain amount of the composition per day, such as the amounts described herein. In other instances, the composition is provided in containers having single servings, and the instructions instruct consumption of a certain number of single servings per day. In both cases an individual following the instructions consumes an amount of soy protein, chromium and free leucine that is effective to inhibit the loss of lean body mass under conditions of caloric restriction. The composition may be sold without the instructions for using the product in the methods of promoting weight loss and/or improving lipid profiles. Instructions can also be provided separately from the sold product, for example posted on a web site.

Some embodiments of the kits further include corosolic acid in any form and in amounts effective to cause subjects to lose weight, such as part of the disclosed soy protein/chromium/free leucine composition or separately. In particular examples the corosolic acid is delivered in a banaba leaf extract that contains 1% corosolic acid, for example as 32 mg of banaba leaf extract that is contained in the supplement.

Example 4

Additional Methods of Promoting Weight Loss

This example discloses the use of compositions in methods of promoting weight loss and/or improvements in the lipid profile of a subject while substantially preserving lean body mass (such as muscle mass). Dosage forms of the composition are administered to deliver desired daily dosages of soy protein, chromium and free leucine, optionally in combination with other agents, while sufficiently restricting caloric intake of the subject to induce weight loss. The composition may be used as a partial meal replacement for the treatment of obesity or hyperlipidemia or other dyslipidemias, for example to reduce blood levels of triglycerides and/or LDL cholesterol and/or the ratio of total cholesterol to HDL.

In particular examples of the methods, the program provides a 500-600 calorie deficit per day leading to losses in body weight of approximately 1-1.5 lb per week. It is particularly suitable for use by overweight, but otherwise healthy, adults. The program components, which may be provided in a kit, include a drink mix, a snack bar, a vitamin/mineral supplement, a tea drink mix, and a 30-day menu/recipe plan (the menu plan serves as a guide for preparing daily meals). In this example, participants follow one of three plans depending on initial body weight:

| Initial Body Weight (lb) | Daily Energy Intake (kcal) |
|---|---|
| <150 | 1200 |
| 150-175 | 1500 |
| >175 | 1800 |

Energy intake throughout the day occurs as follows:

| Breakfast | Drink mix plus fruit |
|---|---|
| Lunch | Drink mix |
| Afternoon | Snack bar +/− food |
| Dinner | Meal |

In this example, the program (products and meals) provides a daily macronutrient distribution range of no more than 30% protein, no more than 50% carbohydrate, and no more than 30% fat. A particular desired range is as follows:

| Macronutrient | % of Energy |
|---|---|
| Protein | 25-30 |
| Carbohydrate | 40-50 |
| Fat | 20-30 |

The dosage forms included in the kit and administered in the method (vitamin/mineral supplement, drink mix, and bar) provide at least 100% of the Daily Value for all essential micronutrients except Vitamins A and K and iron. The meal plan foods contain relatively abundant amounts of these latter nutrients, hence the products plus the menu plan foods are expected to deliver these nutrients in quantities that meet or exceed their required daily amounts.

The daily intake of products containing energy (calorie) content (two drink mixes plus one snack bar) remains the same for all three calorie plans. Additional other calories for the plans are provided by different levels of supplemental food intake. Although free leucine is administered as part of the program, additional protein-bound leucine intake occurs. The method described in this example assumes intake of a 1200 kcal plan.

Free L-leucine that meets food grade and USP specifications is used in both products as an integral component of each mixture and therefore is not separated from the other ingredients (although it can also be administered in a separate product). The drink mix and snack bar contain 1.2 and 0.5 g of added free leucine per serving, respectively. These products also contain a mixture of soy and rice or whey protein isolates (the protein contents of the drink mix and snack bar are 16 and 10 g, respectively). The label instructions advise that the drink mix powder is mixed with one cup of nonfat milk for consumption. Thus, to calculate the total leucine exposure per eating occasion, the amount of free leucine is added to the amount of leucine contained within the protein isolates and nonfat milk as follows:

| Leucine source | Drink mix g/serving | Snack bar g/serving |
|---|---|---|
| Free base | 1.2 | 0.5 |
| Protein isolate | 1.2 | 0.8 |
| Nonfat milk | 0.8 | N/A |
| Total/eating occasion | 3.2 | 1.3 |

In disclosed embodiments the total leucine per eating occasion is about 2.8-3.2 g leucine in the drink (powder dispensed in milk), and about 1.0-1.5 g leucine in the snack bar (inclusive of free leucine and leucine in intact protein).

To calculate the estimated leucine exposure (per eating occasion and daily total), the amount of leucine provided by the meals can also be considered. In this example, the total leucine and protein exposure per day from both products and food is as follows:

|  | Protein (g) | Leucine (g) |
| --- | --- | --- |
| Drink mix (w/nonfat milk) | 24 | 3.2 |
| Snack bar | 10 | 1.3 |
| Food[a] | 38 | 2.8 |
| Daily total[b] | 96 | 10.5 |
|  |  | (2.9 g free base) |

[a]average value determined from 8 menu plan days (1200 kcal plan)
[b]based on recommended plan (sum of two drinks mixed with nonfat milk, one bar and one meal)

Hence, for the 1200 calorie plan, daily totals of protein intake are about 90-100 g protein, and about 8-12 g leucine (of which about 2-4 g are free leucine).

Serving sizes of the drink mix powder and snack bar are approximately 50 and 35 g, respectively.

The total amount of ingested protein-bound leucine can vary depending on the particular plan followed, and this example is not intended to require amounts of leucine that are presented in this example.

Example 5

Promoting Weight Loss with Different Meal Plan

This example discloses an additional use of compositions in methods of promoting weight loss and/or improvements in the lipid profile of a subject while substantially preserving lean body mass (such as muscle mass). Dosage forms of the composition are administered to deliver desired daily dosages of soy protein, chromium and free leucine, optionally in combination with other agents, while sufficiently restricting caloric intake of the subject to induce weight loss. The composition may be used as a partial meal replacement for the treatment of obesity or hyperlipidemia or other dyslipidemias, for example to reduce blood levels of triglycerides and/or LDL cholesterol and/or the ratio of total cholesterol to HDL. The methods of use are the same as in Example 4, except as otherwise specified in the present Example.

In the present Example, the program provides a 600-1000 calorie deficit per day leading to losses in body weight of approximately 1.5-2.0 lb per week. In this example, participants follow one of three plans depending on initial body weight:

| Initial Body Weight (lb) | Daily Energy Intake (kcal) |
| --- | --- |
| <150 | 1200 |
| 151-200 | 1500 |
| 201-250 | 1800 |
| >250 | 2100 |

Energy intake throughout the day occurs as follows:

| Breakfast | Drink mix plus fruit |
| --- | --- |
| Mid-morning | Food (2100 calorie plan only) |
| Lunch | Drink mix |
| Afternoon | Snack bar +/− food (depending on calorie plan) |
| Dinner | Meal |

In this example, the program (products and meals) provides a daily macronutrient distribution range of no more than 30% protein, no more than 45% carbohydrate, and no more than 30% fat. A particular desired range is as follows:

| Macronutrient | % of Energy |
| --- | --- |
| Protein | 25-35 |
| Carbohydrate | 40-45 |
| Fat | 20-30 |

Example 6

Particular Example of Soy/Chromium/Free Leucine Composition

Although many different embodiments of the disclosed products are possible, this example sets forth a particular example of a product that contains useful amounts of soy protein, free leucine and chromium to achieve desired weight reduction with preservation of lean body mass. The following Table 1 shows the distribution of nutrients and active ingredients among the Supplement, Beverage, Tea, and Snack, with active ingredients shown in bold type at the bottom of the table:

TABLE 1

Micronutrient and Other Actives Content of Preparations

| | Per serving | | | | | |
| --- | --- | --- | --- | --- | --- | --- |
| | Shake Mix | Snack | Supplement | Tea | Daily Total[a] | Daily Value |
| Vitamin A (IU) | 500 | 0 | 2500[b] | | 3500 | 70% |
| Vitamin C (mg) | 20 | 0 | 39 | | 79 | 135% |
| Vitamin D (IU) | 140 | 0 | 260 | | 540 | 135% |
| Vitamin E (IU) | 10 | 0 | 20 | | 40 | 135% |
| Vitamin K (μg) | 0 | 0 | 52 | | 52 | 65% |
| Thiamin (mg) | 0.5 | 0.4 | 1.0 | | 2.4 | 160% |
| Riboflavin (mg) | 0.6 | 0.4 | 1.1 | | 2.7 | 160% |
| Niacin (mg) | 7 | 5 | 13 | | 32 | 160% |
| Vitamin B₆ (mg) | 0.7 | 0.5 | 1.3 | | 3.2 | 160% |
| Folate (μg) | 140 | 100 | 260 | | 640 | 160% |
| Vitamin B₁₂ (μg) | 2 | 1.5 | 4 | | 9.5 | 160% |
| Biotin (μg) | 105 | 75 | 195 | | 480 | 160% |
| Pantothenic acid (mg) | 3.5 | 2.5 | 6.5 | | 16 | 160% |
| Calcium (mg) | 350 | 0 | 300 | | 1000 | 100% |
| Iron (mg) | 4.5 | 0 | 0 | | 9 | 50% |
| Phosphorous (mg) | 350 | 0 | 300 | | 1000 | 100% |
| Iodine (μg) | 52.5 | 0 | 97.5 | | 203 | 135% |
| Molybdenum (μg) | 26 | 0 | 49 | | 101 | 135% |
| Selenium (μg) | 24.5 | 0 | 45.5 | | 94.5 | 135% |
| Copper (mg) | 0.7 | 0 | 1.3 | | 2.7 | 135% |
| Manganese (mg) | 0.7 | 0 | 1.3 | | 2.7 | 135% |
| Magnesium (mg) | 140 | 0 | 120 | | 400 | 100% |
| Zinc (mg) | 5.25 | 0 | 9.75 | | 20.25 | 135% |
| Chromium (μg) | 100 | 0 | 400 | | 600 | 500% |
| Banaba Leaf Extract/corosolic acid (mg) | | | | 32/0.32 | 32/0.32 | N/A |
| Vanadium (μg) | | | 100 | | 100 | N/A |
| Taurine (mg) | | | | 800 | 800 | N/A |
| Soy Protein (g) | 14.2-14.4 | 6.9-9.7 | | | 35-39 | N/A |
| Free leucine (g) | 1.2 | 0.5 | | | 2.9 | N/A |

[a]based on recommended product plan (sum of 1 serving of vitamin/mineral supplement, 2 servings of drink mix, 1 serving of tea, and 1 snack bar)
[b]as β-carotene The weight management program, including the normal food suggested in the menu plan, is intended to deliver 10-12 grams of total leucine per day at the 1200 calorie diet plan. The bulk of this leucine (about 8 g) is leucine found in the proteins consumed (from soy protein in the shake and snack bar, milk with which the shake is mixed, and foods/recipes provided in the menu plan). Free leucine added to the shake and bar totals about 2.9 g of this total, but this amount of dietary supplementation with free leucine has been found to provide the unexpectedly superior results of the present invention.

The following Table 2 shows the sources of leucine and protein in a diet that aims for 30% of calories to be derived from protein. In this Table, "other leucine" refers to the leucine that is found within the intact protein (soy and other foods) in each product and food. The food column describes the 1200 kcal plan, and total protein and leucine (protein-bound) amounts will change with higher calorie plans (food menus are provided for 1200, 1500, 1800 and even 2100 cal plans). All these plans include the same number of free leucine-containing products (2 shakes and 1 snack bar) and thus identical amounts of free leucine.

Amounts have been approximated as allowed by food regulations and thus some of the totals appear larger than the sum of the individual components. The Daily Totals also are based on two daily servings of the beverage powder, one serving of tea, one serving of the snack, and one serving of the supplement. Table 2 includes a column for milk because the beverage powder is typically mixed with non-fat milk for each serving. The milk contributes protein and "other leucine (protein-bound)," thus each serving of shake when used as directed delivers 24 g of total protein (including free leucine) and 3.2 g of total leucine of which soy protein comprises 14.3 g and free leucine comprises 1.2 g.

TABLE 2

Sources of leucine and protein in a diet that aims for 30% of calories to be derived from protein

| | Per serving | | | | Daily Total[a] | |
|---|---|---|---|---|---|---|
| | Beverage powder | Milk | Snack Bar | Food | | |
| Soy protein (g) | 14.2-14.4 | — | 7-10 | variable | 35-39 | 90-100 g total protein/day |
| Other protein (g) | <0.5 | 8 | 0-3 | 38 | 57-59 | |
| Free leucine (g) | 1.2 | — | 0.5 | — | 2.9 | 10-12 g total leucine/day |
| Other leucine (g) | 1.2 | 0.8 | 0.8 | 3 | 8 | |

[a]based on recommended product plan (sum of 1 serving of vitamin/mineral supplement, 2 servings of shake, 1 serving of tea, one meal, and 1 snack bar)

Example 7

Example of Drink Mix

In one particular embodiment, a vanilla flavored soy protein/chromium/free leucine beverage powder to be used in the method includes the following specific ingredients shown in Table 3:

TABLE 3

Vanilla flavored soy protein/chromium/free leucine beverage powder

| Ingredients | Weight/Serving (g) | Percent by Weight of Powder (% w/w) |
|---|---|---|
| Soy protein isolate | 16.73 (provides 14.15 g soy protein) | 34.60 (29.27 soy protein) |
| Fructose | 15.05 | 31.13 |
| High oleic sunflower oil powder | 3.16 | 6.54 |
| Acacia gum | 4.85 | 10.04 |
| Canola oil | 0.31 | 0.64 |
| Short chain fructooligosaccharides | 2.00 | 4.14 |
| Leucine | 1.20 | 2.48 |
| Guar gum | 0.20 | 0.41 |
| Dicalcium phosphate | 0.99 | 2.05 |
| Silicon dioxide | 0.52 | 1.08 |
| Sodium citrate | 0.58 | 1.20 |
| Potassium chloride | 0.57 | 1.17 |
| Flavoring | 0.75 | 1.55 |
| Lecithin | 0.55 | 1.14 |
| Whey protein isolate | 0.45 | 0.93 |
| Magnesium oxide | 0.28 | 0.58 |
| Chromium nicotinate | 0.001 (provides 100 μg chromium) | 0.002 |
| Vitamin premix | 0.085 | 0.176 |
| Mineral premix | 0.063 | 0.131 |
| TOTAL | 48.34 | 100.00 |

Example 8

Example of Snack

Although the snack component of the weight management products can take many different forms, a particular example of it is set forth in Table 4. This particular example of the snack is in the form of a snack bar that can be flavored, for example with a chocolate flavor.

TABLE 4

CHOCOLATE FLAVORED SNACK BAR

| Ingredients | Weight/Serving (g) | Percent by Weight of Snack Bar (% w/w) |
|---|---|---|
| Soy protein isolates | 10.42 (provides 8.38 g soy protein) | 33.61 (27.03 soy protein) |
| Leucine | 0.51 | 1.65 |
| Whey protein isolate | 0.90 | 2.90 |
| Fructose | 4.17 | 13.46 |
| Canola oil | 0.47 | 1.50 |
| Acacia gum | 0.34 | 1.10 |
| Guar gum | 0.34 | 1.10 |
| Inulin | 0.95 | 3.05 |
| Vitamin premix | 0.03 | 0.09 |
| Flavorings | 4.69 | 15.13 |
| Sweeteners | 4.94 | 15.92 |
| Medium chain triglycerides | 0.16 | 0.50 |
| Glycerine | 3.10 | 10.00 |
| Total | 31.00 | 100.00 |

Example 9

Supplement Composition

The nutritional supplement is a major source of supplemental chromium in the weight management products and in this example is the sole source of the corosolic acid. A particular example of supplement that serves this purpose is the supplement shown in Table 5, which is administered in a tablet form. The amounts shown in the Table are daily dosages, which in this example are split among three tablets that can be taken at the same time or at different times of the day.

TABLE 5

Supplement Composition

| Ingredients | Weight/Serving (mg) | Percent by Weight of Supplement Tablets (% w/w) |
|---|---|---|
| Magnesium oxide | 219.39 (provides 120 mg magnesium) | 6.80 |
| Zinc gluconate | 80.87 (provides 9.75 mg zinc) | 2.51 |
| Chromium nicotinate | 3.38 (provides 338 μg chromium) | 0.10 |
| Trace mineral protein hydrolysate | 7.53 (provides 62 μg chromium) | 0.23 |
| Banaba leaf extract | 32.00 (provides 0.32 mg corosolic acid) | 1.00 |
| Vanadium amino acid chelate | 4.57 (provides 100 μg vanadium) | 0.14 |
| Other vitamins and minerals | 1,522.13 | 47.21 |
| Herbal blend | 630.20 | 19.55 |
| Other ingredients | 24.07 | 0.75 |
| Excipients | 699.92 | 21.71 |
| Total | 3,224.06 | 100.00 |

The other vitamins and minerals are as described in Table 1.

Example 10

Example of Tea

Some examples of the disclosed product and method provide a tea mix as a source of taurine. The tea mix may be provided in powdered form which is dissolved in water (such as hot water) to produce a tea beverage for consumption. The source of taurine in this example provides 0.98 of the active ingredient, hence the 0.82 g of the taurine source supplies about 0.8 g of taurine.

TABLE 6

Tea mix powder

| Ingredients | Weight/Serving (g) | Percent by Weight of Tea Powder (% w/w) |
|---|---|---|
| Maltodextrin | 0.48 | 28.3 |
| Taurine | 0.82 (provides 0.8 g taurine) | 48.2 |
| Tea extract | 0.29 | 17.2 |
| Green tea powder | 0.02 | 1.2 |
| Flavors | 0.09 | 5.0 |
| Total | 1.70 | 100 |

Example 11

Other Examples of Drink Mix

Two additional embodiments of the soy protein/chromium/free leucine beverage powder to be used in the method include the following specific ingredients shown in Tables 7 and 8. These Examples differ from earlier embodiments in that they remove the whey and short chain fructoologisaccharides and add rice protein concentrate, inulin and more acacia gum.

TABLE 7

Vanilla flavored soy protein/chromium/free leucine beverage powder

| Ingredients | Weight/Serving (g) | Percent by Weight of Powder (% w/w) |
|---|---|---|
| Soy protein isolate | 17.00 (provides 14.38 g soy protein) | 35.10 (29.69 soy protein) |
| Fructose | 15.05 | 31.08 |
| High oleic sunflower oil powder | 3.22 | 6.64 |
| Acacia gum | 6.81 | 14.06 |
| Canola oil | 0.31 | 0.64 |
| Inulin | 0.05 | 0.10 |
| Leucine | 1.20 | 2.48 |
| Guar gum | 0.20 | 0.41 |
| Dicalcium phosphate | 0.99 | 2.05 |
| Silicon dioxide | 0.52 | 1.08 |
| Sodium citrate | 0.58 | 1.20 |
| Potassium chloride | 0.57 | 1.17 |
| Flavoring | 0.75 | 1.55 |
| Lecithin | 0.55 | 1.14 |
| Rice protein concentrate | 0.20 | 0.41 |
| Magnesium oxide | 0.28 | 0.58 |
| Chromium nicotinate | 0.001 (provides 100 μg chromium) | 0.002 |
| Vitamin premix | 0.085 | 0.176 |
| Mineral premix | 0.063 | 0.131 |
| TOTAL | 48.42 | 100.00 |

TABLE 8

Chocolate flavored soy protein/chromium/free leucine beverage powder

| Ingredients | Weight/Serving (g) | Percent by Weight of Powder (% w/w) |
|---|---|---|
| Soy protein isolate | 16.96 (provides 14.35 g soy protein) | 33.42 (28.28 soy protein) |
| Fructose | 16.20 | 31.92 |
| High oleic sunflower oil powder | 2.98 | 5.88 |
| Acacia gum | 6.81 | 13.41 |
| Canola oil | 0.31 | 0.61 |
| Inulin | 0.05 | 0.10 |
| Leucine | 1.20 | 2.36 |
| Cocoa powder | 1.00 | 1.97 |
| Guar gum | 0.20 | 0.39 |
| Dicalcium phosphate | 0.99 | 1.95 |
| Silicon dioxide | 0.52 | 1.03 |
| Sodium citrate | 0.58 | 1.14 |
| Potassium chloride | 0.57 | 1.12 |
| Flavoring | 1.20 | 2.36 |
| Lecithin | 0.55 | 1.08 |
| Rice protein concentrate | 0.20 | 0.39 |
| Magnesium oxide | 0.28 | 0.55 |
| Chromium nicotinate | 0.001 (provides 100 μg chromium) | 0.002 |
| Vitamin premix | 0.085 | 0.168 |
| Mineral premix | 0.063 | 0.125 |
| TOTAL | 50.76 | 100.00 |

Example 12

Other Examples of the Snack

Two additional embodiments of the snack component of the weight management products are set forth in Tables 9 and 10. These particular examples of the snack are in the form of bars that can be flavored, for example with a peanut butter or lemon flavor.

TABLE 9

PEANUT BUTTER FLAVORED SNACK BAR

| Ingredients | Weight/Serving (g) | Percent by Weight of Snack Bar (% w/w) |
|---|---|---|
| Soy protein isolate | 8.68 (provides 6.94 g soy protein) | 28.00 (22.39 soy protein) |
| Leucine | 0.51 | 1.65 |
| Fructose | 3.34 | 10.77 |
| Acacia gum | 0.47 | 1.50 |
| Guar gum | 0.47 | 1.50 |
| Inulin | 1.09 | 3.50 |
| Vitamin premix | 0.03 | 0.09 |
| Flavoring | 7.60 | 24.50 |
| Sweeteners | 7.13 | 23.00 |
| Medium chain triglycerides | 0.16 | 0.50 |
| Glycerine | 1.55 | 5.00 |
| Total | 31.00 | 100.00 |

TABLE 10

LEMON FLAVORED SNACK BAR

| Ingredients | Weight/Serving (g) | Percent by Weight of Snack Bar (% w/w) |
|---|---|---|
| Soy protein isolate | 11.78 (provides 9.68 g soy protein) | 38.00 (31.23 soy protein) |
| Leucine | 0.51 | 1.65 |
| Fructose | 2.87 | 9.27 |
| Soy Fiber | 0.47 | 1.50 |
| Canola oil | 1.78 | 5.75 |
| Acacia gum | 0.54 | 1.75 |
| Guar gum | 0.54 | 1.75 |
| Inulin | 1.16 | 3.75 |
| Vitamin premix | 0.03 | 0.09 |
| Flavoring | 0.87 | 2.80 |
| Sweeteners | 7.44 | 24.00 |
| Color | 0.06 | 0.20 |
| Dried cranberries | 1.24 | 4.00 |
| Medium chain triglycerides | 0.16 | 0.50 |
| Glycerine | 1.55 | 5.00 |
| Total | 31.00 | 100.00 |

Example 13

Use of the Composition

This study example illustrates the use of the disclosed products to help promote weight loss while preserving lean body mass, and/or reduce harmful blood lipid levels. Twenty-seven overweight but otherwise healthy subjects initially participated, of which 13 women and one man completed the 12 week program. Subjects in this study were determined to be clinically overweight as measured by their body mass index. Subjects in the study comprised one group that adhered to a calorically restricted diet as described in Example 4 for 12 weeks. All subjects consumed:
- the drink mix composition of Example 7 containing about 14.2 g of soy protein, 100 µg of chromium, 1.2 g of free leucine, 140 mg of magnesium, and 5.25 mg of zinc for two meals per day, dispensed in non-fat milk;
- a snack bar of Example 8 once per day providing about 8.4 g of soy protein and 0.5 g of free leucine;
- one tablet of the Supplement of Example 9 containing a total dose of about 400 µg of chromium, 32 mg of banaba leaf extract (providing 0.32 mg of corsolic acid), 120 mg of magnesium, 9.75 mg of zinc, and 100 µg of vanadium, taken three times per day (morning, noon and evening) and;
- one serving of the tea mix of Example 10 containing 800 mg of taurine Subjects were instructed to consume one additional meal and any supplemental food per day that provided 540-1140 kcal/day depending on caloric needs. Additionally, subjects were encouraged to engage in exercise and were provided instructions on how to participate in a walking program.

The loss of fat mass and fat-free mass for these subjects was determined from body skinfold measurements, which is a commonly accepted predictor of body fat. Skinfold measurements were made by a single trained observer following standard procedures using Accu-Measure® skinfold calipers (see *ACSM's Guidelines for Exercise Testing and Prescription*, 6th ed. 2000, Philadelphia: Lippincott Williams & Wilkins). Body density was calculated using triceps and subscapular skinfold measurements using the equations of Durnin and Womersley (Br J Nutr, 32(1): p. 77-97, 1974), while percent body fat content was calculated from body density by the Siri's equation (Adv Biol Med Phys, 4: p. 239-80, 1956).

Fat-free mass was determined as the difference between body weight and fat mass. Measurement of body fat from skinfold and dual energy x-ray absorptiometry are well correlated with published correlations of 0.75-0.94.

Waist circumference was measured around the subject's waist along a substantially horizontal line at a point just below the subject's naval with a measuring tape.

A baseline weight, fat mass and fat-free mass was established for each subject, and the subjects were again tested periodically throughout the 12 week program. The amounts of weight, fat mass and fat-free mass at baseline, week 6 and week 12 are presented in the following table as mean±SEM. Analysis of variance (ANOVA) for repeated measures followed by Tukey's post-hoc analysis was used to determine statistical significance and α was set to 0.05.

TABLE 11

Weight Loss Results Using SCL Method and Products

| | Parameter Measured | | |
|---|---|---|---|
| | Baseline | Week 6 | Week 12 |
| Weight (kg) | 84.9 ± 2.9 | 81.1 ± 2.6* | 77.9 ± 2.5* |
| Fat Mass (kg) | 39.7 ± 1.7 | 35.6 ± 1.5* | 32.3 ± 1.5* |
| Fat-Free Mass (kg) | 45.2 ± 1.6 | 45.6 ± 1.6 | 45.7 ± 1.6 |
| Weight Lost (kg) | | 3.8 ± 1.2 | 7.0 ± 2.0 |
| Fat Mass Lost (kg) | | 4.1 ± 0.6 | 7.4 ± 1.0 |
| Fat-Free Mass Gained (kg) | | 0.4 ± 0.3 | 0.5 ± 0.6 |
| Fat-Free Mass Lost | | 0 | 0 |
| Fat-Free Mass Lost as % of Total Weight Lost | | 0% | 0% |
| Ratio of Fat-Free Mass Lost to Fat Mass Lost | | 0% | 0% |
| Waist Circumference Lost (cm) | | 7.4 ± 1.5 | 10.5 ± 1.8 |
| Hip Circumference Lost (cm) | | 5.0 ± 1.2 | 6.5 ± 1.7 |
| Decrease in Waist to Hip Ratio | | 0.03 ± 0.02 | 0.04 ± 0.02 |

Data are presented as ±SEM.
*Indicates P < 0.05.

As can be seen from the results in Table 11, on average subjects lost 7.0 kg over the 12 week period. Subjects lost 7.4 kg of fat mass, and although not statistically significant, gained 0.5 kg of fat-free mass. These data indicate that the weight loss came entirely from body fat and that fat-free mass was preserved throughout the hypocaloric intervention. Waist circumference and hip circumference decreased 10.5 and 6.5 cm, respectively and waist to hip ratio was reduced by 0.04.

At baseline and week 12, plasma triglycerides, total cholesterol, low density lipoprotein and high density lipoprotein were measured for each subject. The decrease in cholesterol, triglycerides and low density lipoprotein (LDL) as well as the increase in high density lipoprotein (HDL) are presented in the table below. A paired student's t-test was used to determine statistical significance and a was set to 0.05.

TABLE 12

Lipid Profile Improvements using SCL Method and Products

| | Parameter Measured | |
|---|---|---|
| | Baseline | Week 12 |
| Triglycerides, mg/dL | 128 ± 18 | 84 ± 7* |
| Percent Decrease in Triglycerides | | 34.4% |
| Total Cholesterol, mg/dL | 209 ± 9 | 187 ± 7* |
| Percent Decrease in Cholesterol | | 10.5% |
| Low Density Lipoprotein, mg/dL | 124 ± 6 | 109 ± 6 |
| High Density Lipoprotein, mg/dL | 60 ± 2 | 62 ± 2 |
| Ratio of total cholesterol to high density lipoprotein | 3.5 ± 0.2 | 3.1 ± 0.1* |

Data are presented as ±SEM.
*Indicates P < 0.05.

These results illustrate there were favorable changes in the blood lipid profiles. There were significant reductions in triglycerides, total cholesterol and the ratio of total cholesterol to HDL. Although total cholesterol decreased and LDL tended to decrease (p=0.05), there was a slight but non-significant increase in HDL (which is generally considered a "protective" cholesterol).

The data in the present Example is further broken down to show body mass changes in two week intervals:

TABLE 13

Weight Lost with SCL Products and Method

| Parameter Measured | Week 2 | Week 4 | Week 6 | Week 8 | Week 10 | Week 12 |
|---|---|---|---|---|---|---|
| Weight Lost (kg) | 1.7 | 2.7 | 3.8 | 4.9 | 6.0 | 7.0 |
| Fat Lost (kg) | 1.7 | NM | 4.1 | NM | 6.3 | 7.4 |
| Fat-Free Mass (kg) | 45.2 | NM | 45.6 | NM | 45.5 | 45.7 |
| Waist Circumference Lost (cm) | 3.7 | 6.3 | 7.4 | 8.9 | 8.7 | 10.5 |
| Hip Circumference Lost (cm) | 2.5 | 4.0 | 5.0 | 6.1 | 6.8 | 6.5 |
| Decrease in Waist to Hip Ratio | 0.01 | 0.02 | 0.03 | 0.03 | 0.02 | 0.04 |

NM = Not Measured

As an added benefit, when asked about the sensation of satiety (feeling of fullness), test subjects responded that they felt satiated. These same subjects also responded positively when questioned about the ability of the program to reduce cravings for food. Subjects particularly noted a reduced craving for carbohydrates. Additionally, these subjects reported feelings of increased energy and vitality while using this product and method.

Example 14

Comparative Data with Prior SS and SSS Trials

The composition and method of Example 13 offers unexpectedly superior preservation of lean body mass in comparison to prior dietary regimens that have included soy protein, chromium or protein-bound leucine.

To demonstrate this superiority, the results of the soy protein/chromium/free leucine (SCL) trial were compared to the compositions and methods disclosed in the assignee's prior U.S. patent application Ser. No. 10/722,368 filed Nov. 24, 2003 and published as US20040166181 on Aug. 26, 2004, as well as in corresponding PCT Publication 04047765 published Jun. 10, 2004. The comparisons were performed between the SCL group and the Supplement plus Spray (SS) or the Supplement plus Spray plus Shake (SSS) groups described in the prior application.

In particular the SS group received the nutritional supplement of Example 6 plus the dietary composition of Example 7 of that prior application. The nutritional supplement of Example 6 of that prior application was two capsules that delivered a total daily dosage of about 32 mg of banaba leaf extract standardized to contain about 1% corosolic acid and about 400 µg chromium in the form of chromium polynicotinate, as well as about 200 mg magnesium, about 5 mg zinc, about 500 mg taurine, about 100 µg vanadium, and about 10 mg alpha lipoic acid. The dietary composition of Example 7 of that prior application was a spray that contained equal amounts of dilutions of about 3× *Fucus vesiculosus*, about 3× *Gambogia garcinia*, about 30 C *Apis mellifica*, about 4× *Badiaga*, about 30× *Calcarea carbonica*, about 3× *Passiflora incamata*, about 12× *Baryta carbonica*, about 12× *Calcarea fluorica*, about 6× *Lycopodium clavatum*, about 6× *Berberis vulgaris*, about 3× *Leptandra virginica*, about 6× *Thuja occidentalis*, about 3× *Galium aparine*, about 30 C *Urtica urens*, about 200 C *Histaminum muriaticum*, and about 30 C *Sabadilla*, which were mixed with about 20% by volume of alcohol and provided in a spray bottle adapted to spray about 0.1-0.5 mL of the dietary composition per spray.

The SSS group in addition received the soy protein/chromium shake drink composition of Example 4 of the prior application. The soy protein/chromium drink of the prior application contained the following ingredients:

| | Prior Shake Drink | |
|---|---|---|
| Ingredients | Percent by Weight of Powder (% w/w) | Weight/Serving |
| Soy Protein Isolate | 29.40 (24.88 soy protein) | 13.91 g (provides 11.77 g soy protein) |
| Fructose | 23.43 | 11.08 g |
| High Oleic Sunflower Oil Powder | 12.68 | 6.00 g |
| *Acacia* Gum | 15.85 | 7.50 g |
| Canola Oil | 2.56 | 1.07 g |
| Inulin | 2.11 | 1.00 g |
| Milk Protein Isolate | 1.90 | 0.90 g |
| Dicalcium Phosphate | 2.10 | 0.99 g |
| Silicon Dioxide | 1.69 | 0.80 g |
| Sodium Citrate | 1.23 | 0.58 g |
| Potassium Chloride | 1.20 | 0.57 g |

-continued

| Ingredients | Prior Shake Drink | |
|---|---|---|
| | Percent by Weight of Powder (% w/w) | Weight/Serving |
| Soy Lecithin | 1.06 | 0.50 g |
| Whey Protein Isolate | 0.95 | 0.45 g |
| Guar Gum | 1.90 | 0.90 g |
| Flavoring | 0.79 | 0.37 g |
| Vitamin Premix | 0.45 | 0.21 g |
| Mineral Premix | 0.37 | 0.18 g (provides 40 μg chromium) |
| Chromium Nicotinate | 0.003 | 1.4 mg (provides 140 μg chromium) |
| Ferrous Fumarate | 0.025 | 11.9 mg |
| Sucralose | 0.0085 | 4.0 mg |
| Mixed Tocopherol Concentrate | 0.002 | 0.9 mg |
| TOTAL | 100.00 | 47.31 g |

The data set forth in Table 14 illustrates the superior preservation of lean body mass with the SCL method of the present invention, as compared to the prior SS Group and SSS Group. In Table 14, the Diet and Exercise group underwent caloric restriction and an exercise regimen without using any weight loss products.

TABLE 14

Comparison of SCL Method to Prior Methods at 12 Weeks of Use

| Parameter Measured | Diet and Exercise | SS Group | SSS Group | SCL Current Trial |
|---|---|---|---|---|
| Weight Lost (kg) | 6.7 | 6.6 | 5.7 | 7.0 |
| Fat Lost (kg)* | 4.5 | 4.4 | 3.8 | 7.4 |
| Lean Body Mass Lost (kg)* | 2.1 | 2.0 | 1.6 | 0 (−0.5) |
| Lean Body Mass Lost as % of Total Body Weight Lost* | 31% | 30% | 28% | 0 |
| Ratio of Lean Body Mass Lost* To Fat Lost | 0.47 | 0.46 | 0.28 | 0 |
| Waist Circumference Lost (cm) | 5.7 | 5.0 | 4.6 | 10.5 |
| Hip Circumference Lost (cm) | 3.8 | 4.5 | 3.7 | 6.5 |
| Decrease in Waist to Hip Ratio | 0.02 | 0.01 | 0.01 | 0.04 |

*Data from the current trial (SCL) are estimates of fat-free mass and fat mass. In the prior study (SS and SSS), lean body mass was measured via DEXA, whereas in the SCL trial skinfold calipers were used to estimate body fat percentage.

Example 15

Prior Protein-Bound Leucine-Containing Diet of Layman et al.

Some prior publications have disclosed the results of studies of the effect of protein-bound leucine on the preservation of lean body mass. Such a study is found, for example, in Layman, et al., J. Nutr. 133:411-417, 2003, in which 24 overweight women (45-56 y old) were divided into two groups of 12 subjects. Both groups consumed isocaloric diets of 1700 cau/day (a 500 cau/day deficit) for 10 weeks. The control diet was fashioned according to the USDA Food Guide Pyramid guide and provided 16% of daily calories from protein (containing 5.4 g of protein-bound leucine per day), 58% from carbohydrate, and 26% from fat. The protein-bound leucine test diet provided 30% of daily calories from proteins containing ample endogenous leucine content such as meats, cheeses and eggs (daily total of roughly 9.9 g protein-bound leucine), 41% carbohydrate, and 29% fat. The table below shows the results obtained with respect to preservation of lean body mass. It is notable that even though the Layman et al. study provided 9.9 g of protein-bound leucine each day, almost 12% of lean body mass was still lost by subjects in that trial. Layman et al. did not administer free leucine; the different amounts of leucine consumed by each group reflected different amounts of dietary protein.

TABLE 15

Weight Loss after 10 Weeks of Higher Protein Diet of Layman et al.

| Parameter Measured | Control Diet (16% protein, 5.4 g protein-bound leucine/day) | Protein Diet (30% protein, 9.9 g protein-bound leucine/day) |
|---|---|---|
| Weight Lost (kg) | 6.96 | 7.53 |
| Fat Lost (kg) | 4.74 | 5.60 |
| Lean Body Mass Lost (kg) | 1.21 | 0.88 |
| Lean Body Mass Lost (% of Total Weight Lost) | 17.4% | 11.7% |
| Ratio of Lean Body Mass Lost to Fat Mass Lost | 0.26 | 0.16 |

Example 16

Comparative Data with Protein-Bound Leucine Containing Diet of Layman et al.

The ratio of lean body mass lost to fat mass lost in the Layman et al. study was 0.16, as compared to substantially zero with the SCL weight management products of the present invention. Similarly, the loss of lean body mass as a percentage of total weight lost was 12% in the Layman et al. diet versus essentially zero in the SCL method. These unexpected and superior results are illustrated in Table 16.

TABLE 16

Weight Loss after 10 Weeks of SCL Method versus Higher Protein Diet of Layman et al.

| Parameter Measured | SCL Method | Protein Diet (30% protein, 9.9 g protein-bound leucine/day) |
|---|---|---|
| Weight Lost (kg) | 6.0 | 7.53 |
| Fat Lost (kg) | 6.3 | 5.60 |
| Lean Body Mass Lost (kg) | 0 (−0.3) | 0.88 |
| Lean Body Mass Lost (% of Total Weight Lost) | 0% | 11.7% |
| Ratio of Lean Body Mass Lost to Fat Mass Lost | 0 | 0.16 |

The above-described examples merely disclose particular, specific embodiments of the disclosed compositions, methods, and kits. They are not intended to be limiting in any way. Moreover, although these embodiments have been described in detail, those of ordinary skill in the art will understand that variations may be made thereto without departing from the spirit of the invention or scope of the appended claims.

We claim:
1. A kit comprising:
a daily dosage of at least

| Ingredient | Amount |
| --- | --- |
| soy protein isolate (g) | 43.88 (providing 36.68 g of soy protein) |
| fructose (g) | 34.27 |
| high oleic sunflower oil (g) | 6.32 |
| Acacia gum (g) | 10.04 |
| canola oil (g) | 1.09 |
| inulin (g) | 0.95 |
| short chain fructooligosacharides (g) | 4 |
| free leucine (g) | 2.91 |
| dicalcium phosphate (g) | 1.98 |
| silicon dioxide (g) | 1.04 |
| sodium citrate (g) | 1.16 |
| potassium chloride (g) | 1.14 |
| lecithin (g) | 1.1 |
| whey protein isolate (g) | 1.8 |
| guar gum (g) | 0.74 |
| flavoring (g) | 6.28 |
| vitamin premix (g) | 0.2 |
| mineral premix (g) | 0.126 |
| chromium (µg) | 600 |
| sweeteners (g) | 4.94 |
| medium chain triglycerides (g) | 0.16 |
| glycerine (g) | 3.1 |
| Banaba leaf extract (mg) | 32 (providing .32 mg of corosolic acid) |
| magnesium oxide (mg) | 779.39 (providing 400 mg of magnesium) |
| zinc gloconate (mg) | 80.87 (providing 9.75 mg of zinc) |
| taurine (mg) | 800 |
| vanadium amino acid chelate | 100 (providing 100 µg vanadium) |
| maltodextrin (g) | .49 |
| tea extract (g) | .29 |
| green tea powder (g) | .02 | wherein the weight ratio of soy protein to free leucine is more than 10:1.

2. The kit of claim 1, wherein the kit comprises multiple dosage forms, wherein the soy protein, chromium and free leucine are each distributed into more than one dosage form.

3. The kit of claim 2, wherein the multiple dosage forms comprise a powdered shake mix, a consumable snack, and a supplement.

4. The kit of claim 3, wherein the multiple dosage forms further comprise a tea preparation.

5. The kit of claim 4, wherein the kit comprises the following dosage forms delivering the following daily dosages:
a shake mix delivering a daily dosage of 33.46 g soy protein from soy protein isolate (providing 28.3 g soy protein), 31 g fructose, 6.32 g high oleic sunflower oil, 9.7 g Acacia gum, 0.62 g canola oil, 4 g fructooligosacharides, 2.4 free leucine, 1.98 g dicalcium phosphate, 1.04 g silicon dioxide, 1.16 g sodium citrate, 1.14 g potassium chloride, 1.1 g lecithin, 0.9 g whey protein isolate, 0.04 g guar gum, 1.5 g flavoring, 0.17 g vitamin premix, 0.126 g mineral premix, 200 µg chromium (provided from 0.002 g of chromium nicotinate), 560 mg magnesium oxide (providing 280 mg magnesium);
a consumable snack delivering a daily dosage of 10.42 g soy protein from soy protein isolate (providing 8.38 g soy protein), 4.17 g fructose, 0.34 g Acacia gum, 0.47 g canola oil, 0.95 g inulin, 0.51 g free leucine, 0.9 g whey protein isolate, 0.34 g guar gum, 4.69 g flavoring, 0.3 g, 4.94 g sweeteners, 0.16 g medium chain triglycerides, 3.1 g glycerine;
a supplement delivering a daily dosage of 400 µg chromium (µg) (provided from 0.00388 g of chromium nicotinate and 0.00753 g mineral protein hydrolysate), 32 mg Banaba leaf extract (providing 0.32 mg of corosolic acid), 219.39 mg magnesium oxide (providing 120 mg magnesium), 80.87 mg zinc gluconate (providing 9.75 mg of zinc), 4.75 mg vanadium amino acid chelate (providing 100 µg vanadium); and
a tea preparation delivering a daily dosage of 0.09 g flavoring flavoring, 800 mg taurine, 0.49 g, 0.29 g tea extract, 0.02 g green tea powder.

6. The kit of claim 5, wherein the daily dosage of the ingredients in the shake mix dosage form is evenly distributed among two shakes.

* * * * *